(12) United States Patent
Gleave

(10) Patent No.: US 7,973,017 B2
(45) Date of Patent: Jul. 5, 2011

(54) TREATMENT OF CANCER BY INHIBITION OF IGFBP'S AND CLUSTERIN

(75) Inventor: Martin Gleave, Vancouver (CA)

(73) Assignee: The University of British Columbia, Vancouver (CA)

(*) Notice: Subject to any disclaimer, the term of this patent is extended or adjusted under 35 U.S.C. 154(b) by 230 days.

(21) Appl. No.: 11/287,334

(22) Filed: Nov. 23, 2005

(65) Prior Publication Data

US 2006/0122141 A1    Jun. 8, 2006

Related U.S. Application Data

(63) Continuation of application No. 10/346,493, filed on Jan. 17, 2003, now abandoned.

(60) Provisional application No. 60/350,046, filed on Jan. 17, 2002, provisional application No. 60/522,948, filed on Nov. 23, 2004, provisional application No. 60/522,960, filed on Nov. 24, 2004.

(51) Int. Cl.
| | |
|---|---|
| A01N 43/04 | (2006.01) |
| C07H 21/02 | (2006.01) |
| C07H 21/04 | (2006.01) |
| C12Q 1/68 | (2006.01) |
| C12P 19/34 | (2006.01) |

(52) U.S. Cl. ......... 514/44; 435/6; 435/91.31; 536/23.1; 536/24.5

(58) Field of Classification Search ........... 435/6, 91.31, 435/91.1, 455; 514/44, 1, 2; 536/23.1, 24.5
See application file for complete search history.

(56) References Cited

U.S. PATENT DOCUMENTS

| | | | |
|---|---|---|---|
| 5,417,978 A | 5/1995 | Tari et al. | |
| 5,646,042 A | 7/1997 | Stinchcomb et al. | |
| 5,721,237 A | 2/1998 | Myers et al. | |
| 5,789,389 A | 8/1998 | Tarasewicz et al. | |
| 5,801,154 A | 9/1998 | Baracchini et al. | |
| 5,855,911 A | 1/1999 | Lopez-Berestein et al. | |
| 5,910,583 A | 6/1999 | Marks et al. | |
| 5,929,040 A | 7/1999 | Werther et al. | |
| 5,998,148 A | 12/1999 | Bennett et al. | |
| 6,133,246 A * | 10/2000 | McKay et al. | 514/44 A |
| 6,172,216 B1 | 1/2001 | Bennett et al. | |
| 6,284,741 B1 | 9/2001 | Werther et al. | |
| 6,335,194 B1 | 1/2002 | Bennett et al. | |
| 6,365,345 B1 | 4/2002 | Brysch et al. | |
| 6,383,808 B1 | 5/2002 | Monia et al. | |
| 6,451,991 B1 | 9/2002 | Martin et al. | |
| 6,900,187 B2 | 5/2005 | Gleave et al. | |
| 7,196,067 B2 * | 3/2007 | Gleave et al. | 514/44 A |
| 2002/0086356 A1 | 7/2002 | Tuschl et al. | |
| 2002/0128220 A1 | 9/2002 | Gleave | |
| 2003/0087857 A1 | 5/2003 | Freier | |
| 2003/0105051 A1 | 6/2003 | McSwiggen | |
| 2003/0158130 A1 * | 8/2003 | Gleave et al. | 514/44 |
| 2003/0158143 A1 | 8/2003 | Gleave et al. | |
| 2003/0166591 A1 | 9/2003 | Gleave et al. | |
| 2004/0006106 A1 | 1/2004 | Uesugi et al. | |
| 2004/0053874 A1 | 3/2004 | Monia et al. | |
| 2004/0096882 A1 | 5/2004 | Gleave et al. | |
| 2004/0220131 A1 | 11/2004 | Jackson et al. | |

FOREIGN PATENT DOCUMENTS

| | | |
|---|---|---|
| WO | WO 92/03470 | 3/1992 |
| WO | WO 92/03471 | 3/1992 |
| WO | WO 00/31048 | 6/2000 |
| WO | WO 00/34469 | 6/2000 |
| WO | WO 00/49937 | 8/2000 |
| WO | WO 00/69454 | 11/2000 |
| WO | WO 00/78341 | 12/2000 |
| WO | WO 01/01748 | 1/2001 |
| WO | WO 01/05435 * | 1/2001 |
| WO | WO 01/46455 A2 | 6/2001 |
| WO | WO 01/75164 | 10/2001 |
| WO | WO 02/22635 A1 | 3/2002 |
| WO | WO 02/22642 | 3/2002 |
| WO | WO 02/44321 * | 6/2002 |
| WO | WO 03/030826 | 4/2003 |
| WO | WO 03/035643 | 5/2003 |
| WO | WO 03/062421 | 7/2003 |
| WO | WO 03/072591 | 9/2003 |
| WO | WO 2004/018675 A1 | 3/2004 |
| WO | WO 2004/018676 A2 | 3/2004 |

OTHER PUBLICATIONS

Opalinska, J. B. et al., Nature Reviews, vol. 1, pp. 503-514 (2002).*
Chirila, T.V. et al., Biomaterials, vol. 23, pp. 321-342 (2002).*
Crooke, S.T., Antisense Res. & Application, Chapter 1, pp. 1-50, Ed. by S. Crooke, Publ. Springer-Verlag (1998).*
Peracchi, A., Rev. Med. Virol., vol. 14, pp. 47-64 (2002).*
Agrawal, S. et al., Molecular Med. Today, vol. 6, pp. 72-81 (2000).*
Branch, A.D., Trends in Biochem. Sci., vol. 23, pp. 45-50 (1998).*
Crooke, S., Ann. Rev. Medicine, vol. 55, pp. 61-95 (2004).*
Peracchi et al., Rev. Med. Virol., vol. 14, pp. 47-64 (2004).*
Agrawal et al., Molecular Med. Today, vol. 6, pp. 72-81 (2000).*
Chirila et al., Biomaterials, vol. 23, pp. 321-342 (2002).*
Opalinska et al., Nature Rev., vol. 1, pp. 503-514 (2002).*
Holen et al., Nucleic Acids. Res., vol. 30, No. 8, pp. 1757-1766 (2002).*
Jang, J.-H. et al., Gene delivery from polymer scaffolds for tissue engineering, Expert Rev. Med. Devices, vol. 1, No. 1, pp. 127-138 (2004).*
Crooke, S., Progress in antisense technology, Ann. Rev. Medicine, vol. 55, pp. 61-95 (2004).*
Agrawal, S. et al., Antisense therapeutics: Is it as simple as complementary base recognition? Molecular Med. Today, vol. 61, pp. 72-81 (2000).*

(Continued)

Primary Examiner — Jane Zara
(74) Attorney, Agent, or Firm — Larson & Anderson, LLC

(57) ABSTRACT

Agents that reduce the amount of IGFBP-2 and/or IGFBP-5 and that are known to be useful in the treatment of cancer result in increased expression of the protein clusterin. Since clusterin can provide protection against apoptosis, this secondary effect detracts from the efficacy of the therapeutic agent. In overcoming this, the present invention provides a combination of therapeutic agents that is useful in the treatment of cancer. The combination includes an agent that reduces the amount of IGFBP-2 and/or IGFBP-5 and that stimulates expression of clusterin as a secondary effect, and an oligonucleotide that is effective to reduce the amount of clusterin in cancer cells. In some embodiments of the invention, the agent that reduces IGFBP-2 and/or IGFBP-5 is a bispecific antisense species. The oligonucleotide may be an antisense oligonucleotide or an RNAi oligonucleotide.

21 Claims, 13 Drawing Sheets

OTHER PUBLICATIONS

Opalinska, J.B. et al., Nucleic acid therpaeutics: Basic principles and recent applications. Nature Rev., vol. 1, pp. 503-513 (2002).*

Binkert, et al., Structure of the Human Insulin-Like Growth Factor Binding Protein-2 Gene, Molecular Endocrinology, 1992, pp. 826-836, vol. 6, No. 5.

Bubendorf, et al., Hormone Therapy Failure in Human Prostate Cancer: Analysis by Complementary DNA and Tissue Microarrays, Journal of the National Cancer Institute, Oct. 20, 1999, pp. 1758-1764, vol. 91, No. 20.

Corkins et al., Growth Stimulation by Transfection of Intestinal Epithelial Cells with an Antisense Insulin-Like Growth Factor Binding Protein-2 Construct, Biochemical and Biophysical Research Communications, Jun. 26, 1995, pp. 707-713, vol. 211, No. 3.

Forsyth, et al., Growth Inhibition of a Human Colon Cancer Cell Line by Antisense Oligonucleotide to IGFBP-2, 1995, p. A726, vol. 108, No. 4.

Gleave, et al., Antisense Targets to Enhance Hormone and Cytotoxic Therapies in Advanced Prostate Cancer, Current Drug Targets, 2003, pp. 209-221, vol. 4, No. 3.

Miyake, et al., Castration-Induced Up-Regulation of Insulin-Like Growth Factor Binding Protein-5 Potentiates Insulin-Like Growth Factor-I Activity and Accelerates Progression to Androgen Independence in Prostate Cancer Models, Cancer Research, Jun. 1, 2000, pp. 3058-3064, vol. 60.

Steller et al., Insulin-like growth factor II mediates epidermal growth factor-Induced mitogenesis in cervical cancer cells, Proc. Natl. Acad. Sci.-Cell Biology, Dec. 1995, pp. 11970-11974, vol. 92.

Wang et al., Correlation of Glioma Cell Regression with Inhibition of Insulin-Like Growth Factor 1 and Insulin-Like Growth Factor-Binding Protein-2 Expression, Neuroendrocrinology, 1997, pp. 203-211, vol. 66.

Shimasaki et al., Identification of Five Different InsulIn-like Growth Factor Binding Proteins (IGFBP's) from Adult Rat Serum and Molecular Cloning of a Novel IGFBP-5 in Rat and Human, Journal of Biological Chemistry, Jun. 5, 1991, pp. 10646-10653, vol. 266, No. 16.

Zangemeister-Wittke et al., A Novel Bispecific Antisense Oligonucleotide Inhibiting both bcl-2 and bcl-xL Expression Efficiently Induces Apoptosis in Tumor Cells, Clinical Cancer Research: An Official Journal of the American Association for Cancer Research, Jun. 2000, pp. 2547-2555, vol. 6, No. 6.

Andress et al. , Human Osteoblast-derived Insulin-like Growth Factor (IGF) Binding Proteln-5 Stimulates Osteoblast Mitogenesis and Potentiates IGF Action, Journal of Biological Chemistry, Nov. 5, 1992, pp. 22467-22472, vol. 267, No. 31.

Andrea D. Branch, A good antisense molecule is hard to find, TIBS, Feb. 1998, pp. 45-50.

Crooke et al., Basic Principles of Antisense Therapeutics, Antisense Research and Application, 2004, pp. 1-50, Publisher: Springer.

Jen et al., Suppression of Gene Expression by Targeted Disruption of Messenger RNA: Available Options and Current Strategies, Stem Cells 2000, 2000, pp. 307-319, vol. 18.

Opalinska et al., Nucleic-acid therapeutics: Basic principles and recent applications, Nature Reviews, Jul. 2002, pp. 503-514, vol. 1.

Agrawal et al., Antisense therapeutics: is it as simple as complementary base recognition?, Molecular Medicine Today, Feb. 2000, pp. 72-81, vol. 6.

Angelloz-Nichoud et al., Autocrine Regulation of Cell Proliferation by the Insulin-Like Growth Factor (IGF) and IGF Binding Protein-3 Protease System in a Human Prostate Carcinoma Cell Line (PC-3), Endocrinology, 1995, pp. 5485-5492, vol. 136, No. 12.

Boudon et al., Secretion of Insulin-Like Growth Factors and Their Binding Proteins by Human Normal and Hyperplastic Prostatic Cells in Primary Culture, Journal of Clinical Endocrinology and Metabolism, Feb. 1, 1996, pp. 612-617, vol. 81, No. 2.

Cucco et al., In Vitro and In Vivo Reversal of Multidrug Resistance in a Human Leukemia-resistant Cell Line by mdr1Antisense Oligodeoxynucleotides, Cancer Research, Oct. 1, 1996, pp. 4332-4337, vol. 56.

Elgin et al., An insulin-like growth factor (IGF) binding protein enhances the biologic response to IGF-I, Cell Biology, May 1987, pp. 3254-3258, vol. 84, Publisher: Proc. Natl. Acad. Sci.

Figueroa et al., Differential Expression of Insulin-Like Growth Factor Binding Proteins in High Versus Low Gleason Score Prostate Cancer, The Journal of Urology, Apr. 1998, pp. 1379-1383, vol. 159, No. 4.

Huynh et al., Estradiol and Antiestrogens Regulate a Growth Inhibitory Insulin-like Growth Factor Binding Protein 3 Autocrine Loop in Human Breast Cancer Cells, The Journal of Biological Chemistry, Jan. 12, 1996, pp. 1016-1021, vol. 271, No. 2.

Jansen et al., bcl-2 antisense therapy chemosensitizes human melanoma in SCID mice, Nature Medicine, Feb. 1998, vol. 4, No. 2.

Monia et al., Antitumor Activity of a Phosphorothioate Antisense Oligodeoxynucieotide Targeted against C-raf Kinase, Nature Medicine, Jun. 1996, pp. 668-675, vol. 2, No. 6.

Nickerson et al., Castration-induced apoptosis in the rat ventral prostate is associated with increased expression of genes encoding insulin-like growth factor binding proteins 2,3,4 and 5, Endocrinology, 1998, pp. 807-810, vol. 139, No. 2.

Oh et al., Mangagement of Hormone Refractory Prostate Cancer: Current Standards and Future Prospects, The Journal of Urology, Oct. 1998, pp. 1220-1229, vol. 160, No. 4.

Oh et al., Insulin-like Growth Factor (IGF)-independent Action of IGF-binding Protein-3 in Hs578T Human Breast Cancer Cells, The Journal of Biological Chemistry, Jul. 15, 1993, pp. 14964-14971, vol. 268, No. 20.

Rajaram, Insulin-Like Growth Factor-Binding Proteins in Serum and Other Biological Fluids: Regulation and Functions, Endocrine Reviews, 1997, pp. 801-831, vol. 18, No. 6.

Damon, et al., Overexpression of an Inhibitory Insulin-Like Growth Factor Binding Protein (IGFBP), IGFBP-4, Delays Onset of Prostate Tumor Formation, Endocrinology, 1998, pp. 3456-3464, vol. 139, No. 8.

Ziegler et al., Induction of Apoptosis in Small-Cell Lung Cancer Cells by an Antisense Oligodeoxynucleotide Targeting the Bcl-2 Coding , Journal of National Cancer Institute, Jul. 16, 1997, vol. 89, No. 14.

Levitt Jr. et al., Bispecific antisense oligonucleotide targeting both IGFBP-2 and IGFBP-5 inhibits growth of U87 glioma cells, Growth Hormone & IGF Research, Apr. 2004, p. 118, vol. 14, No. 2.

Zumkeller, IGFs and IGF-binding proteins as diagnostic markers and biological modulators in brain tumors, Expert Rev Mol Diagn., 2002, pp. 473-477, vol. 2, No. 5.

Bruchovsky et al., Classification of Dependent and Autonomous Variants of Shionogi Mammary Carcinoma Based on Heterogenous Patterns of Androgen Binding, Cell, Feb. 1978, pp. 273-280, vol. 13.

Bruchovsky et al., Effects of Androgen Withdrawal on the Stem Cell Composition of the Shionogi Carcinoma, Cancer Research, Apr. 15, 1990, pp. 2275-2282, vol. 50.

Gleave et al., Serum Prostate Specific Antigen Levels in Mice Bearing Human Prostate LNCaP Tumors Are Determined by Tumor Volume and Endocrine and Growth Factors, Cancer Research, Mar. 15, 1992, pp. 1598-1605, vol. 52.

Gleave et al., Animal Models in Prostate Cancer, Principles and Practice of Genitourinary Oncology, 1997, pp. 367-378, Publisher: Lippincott-Raven; Editors: Raghavan et al.

Gleave et al., Intermittent Androgen Suppression for Prostate Cancer: Rationale and Clinical Experience, European Urology, 1998, pp. 37-41, vol. 34; Suppl. 3.

Gleave et al., Prostate cancer: 9. Treatment of advanced disease, Canadian Medical Association Journal, Jan. 26, 1999, pp. 225-232, vol. 160, No. 2.

Gleave et al., Neoadjuvant Androgen Withdrawal Therapy Decreases Local Recurrence Rates Following Tumor Excision in the Shionogi Tumor Model, The Journal of Urology, May 1997, pp. 1727-1730, vol. 157, No. 5.

James et al., A Highly Conserved Insulin-like Growth Factor-binding Protein (IGFBP-5) Is Expressed during Myoblast Differentiation, The Journal of Biological Chemistry, Oct. 25, 1993, pp. 22305-22312, vol. 268, No. 30.

Kiefer et al., Molecular Cloning of a New Human Insulin-like Growth Factor Binding Protein, Biochemical and Biophysical Research Communications, Apr. 15, 1991, pp. 219-225, vol. 176, No. 1.

Miyake et al., Overexpression of Insulin-like Growth Factor Binding Protein-5 Helps Accelerate Progression to Androgen-independence in the Human Prostate LNCaP Tumor Model through Activation of Phosphatidylinositol 3'-Kinase Pathway, Endocrinolgy, 2000, pp. 2257-2265, vol. 141, No. 6.

Rennie et al., Gene Expression during the Early Phases of Regression of the Androgen-dependent Shionogi Mouse Mammary Carcinoma, Cancer Research, Nov. 15, 1988, pp. 6309-6312, vol. 48.

American Cancer Society, Cancer Facts & Figures 2004, 2004, pp. 1-56, Publisher: American Cancer Society.

Johnson et al., Quality of long-term survival in young children with medulloblastoma, J Neurosurg, Jun. 1994, pp. 1004-1010, vol. 80.

Lallana et al., Update on the therapeutic approaches to brain tumors, Expert Rev. Anticancer Ther., 2003, pp. 655-670, vol. 3, No. 5.

Mahaley et al., National survey of patterns of care for brain-tumor patients, J Neurosurg, Dec. 1989, pp. 826-836, vol. 71.

Packer et al., A prospective study of cognitive function in children receiving whole-brain radiotherapy and chemotherapy: 2-year results, J Neurosurg, May 1989, pp. 707-713, vol. 70.

Parkin et al., Estimating the World Cancer Burden: Globocan 2000, Int. J. Cancer, 2001, pp. 153-156, vol. 94.

National Cancer Institute, Trends in SEER Incidence and U.S. Mortality Using the Joinpoint Regression Program, 1975-2000 With Up to Three Joinpoints By Race and Sex, SEER Cancer Statistics Review 1975-2000, 2000, Publisher: National Cancer Institute.

Strother et al., Tumors of the Central Nervous System, Principles and Practice of Pediatric Oncology, $4^{th}$ Edition, Editors: Pizzo et al., 2002, pp. 751-824, Publisher: Lippincott Williams & Wilkins.

Surawicz et al., Brain tumor survival: Results from the National Cancer Data Base, Journal of Neuro-Oncology, 1998, pp. 151-160, vol. 40.

Gleave et al., Targeting anti-apoptotic genes upregulated by androgen withdrawal using antisense oligonucleotides to enhance androgen- and chemo-sensitivity in prostate cancer, Investigational New Drugs, 2002, pp. 145-158, vol. 20.

Gleave et al., Use of Antisense Oligonucleotides Targeting the Antiapoptotic Gene, Clusterin/Testosterone-Repressed Prostate Message 2, To Enhance Androgen Sensitivity and Chemosensitivity in Prostate Cancer, Urology, 2001, pp. 39-49, vol. 58, XP-002262320.

Gleave et al., Antisense therapy: Current status in prostate cancer and other malignancies, Cancer and Metastasis Reviews, 2002, pp. 79-92, vol. 21.

Gleave et al., Antisense Targets to Enhance Hormone and Cytotoxic Therapies in Advanced Prostate Cancer, Current Drug Targets, 2003, pp. 209-221, vol. 4, XP-009021409.

Jones et al., Molecules in focus: Clusterin, The International Journal of Biochemistry & Cell Biology, 2002, pp. 427-431, vol. 34.

Miyake et al., Antisense TRPM-2 Oligodeoxynucleotides Chemosensitize Human Androgen-Independent PC-3 Prostate Cancer Cells Both in Vitro and in Vivo, Clinical Cancer Research, 2000, pp. 1655-1663, vol. 6, XP-000960694.

Miyake et al., Testosterone-repressed Prostate Message-2 Is an Antiapoptofic Gene Involved in Progression to Androgen Independence in Prostate Cancer, Cancer Research, 2000, pp. 170-176, vol. 60, XP-002907064.

Miyake et al., Synergistic Chemsensitization and Inhibition of Tumor Growth and Metastasis by the Antisense Oligodeoxynucleotide Targeting Clusterin Gene in a Human Bladder Cancer Model, Clinical Cancer Research, 2001, pp. 4245-4252, vol. 7, XP-002263075.

Miyake et al., Novel therapeutic strategy for advanced prostate cancer using antisense oligodeoxynucleotides targeting antiapoptotic genes upregulated after androgen withdrawal to delay androgen-independent progression and enhance chemosensitivity, International Journal of Urology, 2001, pp. 337-349, vol. 8, XP-002262321.

Sensibar et al., Prevention of Cell Death Induced by Tumor Necrosis Factor a in LNCaP Cells by Overexpression of Sulfated Glycoprotein-2 (Clusterin), Cancer Research, 1995, pp. 2431-2437, vol. 55, XP-002930082.

Rosenberg et al., Clusterin: Physiologic and Pathophysiologic Considerations, Int. J. Biochem. Cell Biol., 1995, pp. 633-645, vol. 27, No. 7, XP-001002844.

Wilson et al., Clusterin is a secreted mammalian chaperone, TIBS, 2000, pp. 95-97, vol. 25.

Wong et al., Molecular characterization of human TRPM-2/clusterin, a gene associated with sperm maturation, apoptosis and neurodegeneration, Eur. J. Biochem, 1994, pp. 917-925, vol. 91, XP-001146404.

Green et al., Antisense Oligonucleotides: An Evolving Technology for the Modulation of Gene Expression in Human Disease, J Am Coll Surg, Jul. 2000, vol. 191, No. 1, pp. 93-105.

Zellweger et al., Antitumor Activity of Antisense Clusterin Oligonucleotides is Improved in Vitro and in Vivo by Incorporation of 2'O'(2-Methoxy)Ethyl Chemistry, The Journal of Pharmacology and Experimental Therapeutics, 2001, pp. 934-940, vol. 298, No. 3, XP-002262318.

Zellweger et al., Chemosensitization of Human Renal Cell Cancer Using Antisense Oligonucleotides Targeting the Antiapoptotic Gene Clusterin, Neoplasia, 2001, pp. 360-367, XP-009004604.

Chako et al., Double-stranded ribonucleic acid decreases C6 rat glioma cell numbers: Effects on insulin-like growth factor I gene expression and action, Endocrinology, Oct. 2000, vol. 141, No. 10, pp. 3546-3555.

Pavelic et al., Insulin-Ike growth factor family and combined antisense approach in therapy of lung carcinoma, Molecular Medicine, Mar. 2002, vol. 8, No. 3. pp. 149-157.

Aoki et al., RNA Intereference may be more potent than antisense RNA in human cancer cell lines, Clinical and Experimental Pharmacology and Physiology, 2003, pp. 96-102.

Benner et al., Combination of Antisense Oligonucleotide and Low-Dose Chemotherapy in Hematological Malignancies, Journal of Pharmacological and Toxicological Methods, 1997, pp. 229-235, Publisher: Elsevier Science Inc.

Boral et al., Clinical evaluation of biologically targeted drugs: obstacles and opportunities, Cancer Chemother Pharmacol, 1998, pp. S3-S21, Publisher: Springer-Verlag.

Steven Brem, MD, Angiogenesis and Cancer Control: From Concept to Therapeutic Trial, Cancer Control Journal, 1999, vol. 6, No. 5, Publisher: H. Lee Moffitt Cancer Center & Research Institute.

Bruchovsky et al., Control of Tumor Progression by Maintenance of Apoptosis, www.prostatepointers.org, 1996, Publisher: Wiley-Liss, Inc.

Buttyan et al., Induction of the TRPM-2 Gene in Cells Undergoing Programmed Death, Molecular and Cellular Biology, 1989, pp. 3473-3481, vol. 9, No. 8, Publisher: American Society for Microbiology.

Cox et al., Angiogenesis and non-small cell lung cancer, Lung Cancer, 2000, pp. 81-100, Publisher: Elsevier.

Darby et al., Vascular Expression of Clusterin in Experimental Cyclosporine Nephrotoxicity, Exp Nephrol, 1995, pp. 234-239, Publisher: S. Karger AG.

Diemer et al., Expression of Porcine Complement Cytolysis Inhibitor mRNA in Cultured Aortic Smooth Muscle Cells, The Journal of Biological Chemistry, Mar. 15, 1992, pp. 5257-5264, vol. 207, No. 8, Publisher: The AMerican Society for Biochemistry and Molecular Biology, Inc.

Genta, New Data Reaffirm Genta's Molecular Target as Critical Factor for Enhancing Anticancer Treatment, www.genta.com, 2001.

Kadomatsu et al., Expression of sulfated glycoprotein 2 is associated with carcinogenesis induced by N-nitroso-N-methylurea in rat prostat, Cancer Res, Apr. 1, 1993, pp. 1480-1483, vol. 53, No. 7.

Kirby et al., Bartonella-associated endothelial proliferation depends on inhibition of apoptosis, PNAS, Apr. 2, 2002, pp. 4656-4661, vol. 99, No. 7.

Kyprianou et al., bcl-2 over-expression delays radiation-induced apoptosis without affecting the clonogenic survival of human prostate, International Journal of Cancer, Jan. 27, 1997, pp. 341-348, vol. 70, No. 3.

Lee et al., In Vitro Models of Prostate Apoptosis: Clusterin as an Antiapoptotic Mediator, The Prostate Supplement, 2000, pp. 21-24, vol. 9, Publisher: Wiley-Liss, Inc.

Millar et al., Localization of mRNAs by in-situ hybridization to the residual body at stages IX-X of the cycle of the rat seminiferous, International Journal of Andrology, 1994, pp. 149-160, vol. 17.

Millis et al., Clusterin Regulates Vascular Smooth Muscle Cell Nodule Formation and Migration, Journal of Cellular Physiology, 2001, pp. 210-219, vol. 186, Publisher: Wiley-Liss, Inc.

Milner et al., Selecting effective antisense reagents on combinatorial oligonucleotide arrays, Nature Biotechnology, 1997, pp. 537-541, vol. 15.

Nor et al., Engineering and Characterization of Functional Human Microvessels in Immunodeficient Mice, Laboratory Investigation, 2001, pp. 453-463, vol. 81, No. 4.

Nor et al., Up-Regulation of Bcl-2 in Microvascular Endothelial Cells Enhances Intratumoral Angiogenesis and Accelerates Tumor Growt, Cancer Research, Mar. 1, 2001, pp. 2183-2188, vol. 61.

Tran et al., A role for survivin in chemoresistance of endothellal cells mediated by VEGF, PNAS, Apr. 2, 2002, pp. 4349-4354, vol. 99, No. 7.

Trougakos et al., Silencing Expression of the Clusterin/Apolipoprotein J Gene in Human Cancer Cells Using Small Interfering RNA Induces, Cancer Research, Mar. 1, 2004, pp. 1834-1842, vol. 64.

Vickers et al., Efficient Reduction of Target RNAs by Small Interfering RNA and RNase H-dependent Antisense Agents, The Journal of Biological Chemistry, Feb. 28, 2003, pp. 7103-7118, vol. 278, No. 9.

Wright et al., A ribonucleotide reductase Inhibitor, MDL 101,731, induces apoptosis and elevates TRPM-2 mRNA levels in human prostate, Experimental Cell Research, Jan. 10, 1996, pp. 54-60, vol. 222, No. 1.

Yang et al., Nuclear clusterin/XIP8, an x-ray-induced Ku70-binding protein that signals cell death, PNAS, May 23, 2000, pp. 5907-5912, vol. 97, No. 11.

Zwain et al., Clusterin Protects Granulosa Cells from Apoptotic Cell Death during Follicular Atresia, Experimental Cell Research, 2000, pp. 101-110, vol. 257, Publisher: Academic Press.

Carthew et al, Gene silencing by double-stranded RNA, Current Opinion in Cell Biology, 2001, pp. 244-248, vol. 13.

Demattos et al., Clusterin promotes amyloid plaque formation and is critical for neuritic toxicity in a mouse model of Alzheimer's diseas, PNAS, Aug. 6, 2002, pp. 10843-10848, vol. 99, No. 16.

Elbashir et al., Duplexes of 21-nucleotide RNAs mediate RNA interference in cultured mammalian cells, Nature, May 24, 2001, pp. 494-498, vol. 411.

Fire et al., Potent and specific genetic interference by double-stranded RNA in Caenorhabditis elegans, Nature, Feb. 19, 1998, pp. 806-811, vol. 391.

Tamm et al., Antisense therapy in oncology: new hope for an old idea?, The Lancet, pp. 489-497, vol. 358, No. 9280, 2001.

Agrawal, Antisense oligonucleotides: towards clinical trials, TIBTECH, Oct. 1996, pp. 376-387, vol. 14.

Gewirtz et al., Facilitating oligonucleotide delivery: Helping aintisense deliver on its promise, Proc. Natl. Acad. Sci., Apr. 1996, pp. 3161-3163, vol. 93.

Gregory, Androgen Receptor Up-Regulates Insulin-Like Growth Factor Binding Protein-5 (IGFBP-5) Expression in a Human Prostate Cancer Xenograft, Enocrinology, 1999, pp. 2372-2381, vol. 140, No. 5.

Huynh et al., A Role for Insulin-like Growth Factor Binding Protein 5 in the Antiproliferative Action of the Antiestrogen ICI 182780, Cell Growth and Differentiation, Nov. 1996, pp. 1501-1506, vol. 7.

Nickerson et al., Castration-induced Apoptosis of Androgen-dependent Shionogi Carcinoma Is Associated with Increased Expression of Genes, Cancer Research, Jul. 15, 1999, pp. 3392-3395, vol. 59.

Reuters, Lilly, Isis Antisense Drug Fails in Trial, News Release, Mar. 17, 2003.

Davies et al., Mutations of the BRAF gene in human cancer, Nature, , pp. 949-954, vol. 417, 2002.

Gewirtz, A Critical Evaluation of the Mechanisms of Action Proposed for the Antitumor Effects of the Anthracycline Antibiotics, Biochemical Pharmacology, , pp. 727-741, vol. 57, 1999.

Harborth et al., Identification of essential genes in cultured mammalian cells using small interfering RNAs, Journal of Cell Science, pp. 4557-4565, vol. 114, 2001.

Leskov et al., Synthesis and Functional Analyses of Nuclear Clusterin, a Cell Death Protein, The Journal of Biological Chemistry, , pp. 11590-11600, vol. 278, No. 13, 2003.

McGill et al., Bcl2 Regulation by the Melanocyte Master Regulator Mitf Modulates Lineage Survival and Melanoma Cell Viability, Cell, , pp. 707-718, vol. 109, 2002.

Muller et al., Cellular pharmacokinetics of doxorubicin in patients with chronic lymphocytic leukemia: comparision of bolus administr . . . , Cancer Chemother Pharmacol, , pp. 379-384, vol. 32, 1993.

Rohlff et al., Prostate Cancer Cell Growth Inhibition by Tamoxifen Is Associated With Inhibition of Protein Kinase C and Induction of . . . , The Prostate, , pp. 51-59, vol. 37, 1998.

Agami, RNAi and related mechanisms and their potential use for therapy, Current Opinion in Chemical Biology, , pp. 829-834, vol. 6, Publisher: Current Biology Ltd, London, GB XP00295888, 2002.

Brummelkamp et al., A system for stable expression of short interfering RNAs in mammalian cells, Science, , pp. 550-553, vol. 296, No. 5567, Publisher: American Association for the Advancement of Science, US, 2002.

Calero et al., Apolipoprotein J (Clusterin) and Alzheimer's Disease, Microscopy Research and Technique, , pp. 305-315, vol. 50, No. 4, Publisher: XP009021345, 2000.

Choi-Miura et al., Relationship Between Multifunctional Protein "Clusterin" and Alzheimer Disease, Neurobiology of Aging, , pp. 717-722, vol. 17, No. 5, Publisher: XP001146408, 2004.

Demir et al., Use of RNA interference (RNAi) to Disrupt C-Kit Gene Expression in Malignant Human Hematopoietic and Neuroepithellal . . . , Blood, , p. 378B, vol. 96, No. 11, Part 2, Publisher: W. B. Saunders Company, Orlando, FL, US XP009004894, 1999.

EMBL accession No. M63376, Jul. 1991.

Hohjoh, RNA interference (RNAi) induction with various types of synthetic oligonucleotide duplexes in cultered human cells, FEBS Letters, pp. 195-199, vol. 521, No. 1-3, Publisher: Elsevier Science Publishers, Amsterdam, NL XP004362164, 2002.

Koch-Brandt et al., Clusterin: A Role in Cell Survival in the Face of Apoptosis?, Progress in Molecular and Subcellular Biology, , pp. 130-149, vol. 16, Publisher: XP009021385, 1996.

Paddison et al., Stable suppression of gene expression by RNAi in mammalian cells, Proceedings of the National Academy of Sciences of USA, pp. 1443-1448, vol. 99, No. 3, Publisher: National Academy of Science, XP002958887, 2002.

Sharp, RNAi and double-strand RNA, Genes and Development, , pp. 139-141, vol. 13, No. 2, Publisher: Cold Spring Harbor Laboratory Press, New York, US, XP002171268, 1999.

Strocchi et al., Neuronal loss up-regulates clusterin mRNA in living neurons and glial cells in the rat brain, NeuroReport, , pp. 1789-1792, vol. 10, No. 8, Publisher: Rapid Communications of Oxford, Oxford, GB, XP009017327, 1999.

Sui et al., A DNA vector-based RNAi technology to suppress gene expression in mammalian cells, Proceddings of the National Academy of Sciences of USA, , pp. 5515-5520, vol. 99, No. 8, Publisher: National Academy of Science, Washington, US, XP002964701, 2002.

Tuschl et al., Targeted mRNA degradation by double-stranded RNA in vitro, Genes and Development, , pp. 3191-3197, vol. 13, No. 24, Publisher: Cold Spring Harbor Laboratory Press, New York, US, XP002183118, 1999.

Ueda, RNAi: A new technology in the post-genomic sequencing era, Journal of Neurogenetics, , pp. 193-204, vol. 15, No. 3/4, Publisher: Elsevier, Amsterdam, NL, XP001147227, 2001.

Baxevanis et al., Immunobiology of HER-2/neu oncoprotein and its potential in cancer Immunotherapy, Cancer Immunol. Immunother., 2004, pp. 166-175, vol. 53.

Bellmunt et al., Novel approaches with targeted therapies in bladder cancer. Therapy of bladder cancer by blockade of the epidermal, Crit. Rev. Oncol. Hematol., 2003, pp. S85-S104, vol. 46 Suppl.

Cianciulli et al., Her-2/neu oncogene amplification and chromosome 17 aneusomy in endometrial carcinoma: correlation with oncoprotein, J. Exp. Clin. Cancer Res., 2003, pp. 265-271, vol. 22.

Di Lorenzo et al., Her-2/neu receptor in prostate cancer development and progression to androgen independence, Tumori, 2004, pp. 163-170, vol. 90.

Half et al., Her-2/neu receptor expression, localization and activation in colorectal cancer cell lines and human tumors, Int. J. cancer, 2004, pp. 540-548, vol. 108.

Lazebnik et al., Cleavage of poly (ADP-ribose) polymerase by a proteinase with properties like ICE, Nature, Sep. 22, 1994, pp. 346-347, vol. 371.

Nathanson et al., HER-2/neu expression and gene amplification in colon cancer, Int. J. cancer, 2003, pp. 796-802, vol. 105.

Park et al., Clinical significance of HER-2/neu expression in colon cancer, Korean J. Gastroenterol., 2004, pp. 147-152, vol. 44.

Scholl et al., Targeting HER-2 in other tumor types, Annals of Oncology, 2001, pp. S81-S87, vol. 12, Suppl 1.

Slamon et al, Use of chemotherapy plus a monoclonal antibody against HER2 for metastatic breast cancer that overexpresses HER2, NEJM, 2001, pp. 783-792, vol. 344, No. 11.

Slomovitz et al., Her-2/neu overexpression and amplification in uterine papillary serous carcinoma, J. Clin. Oncol., 2004, pp. 3126-3132, vol. 22.

Telford et al., Comparative evaluation of several DNA binding dyes in the detection of apoptosis-associated chromatin degradation, Cytometry, , pp. 137-143, vol. 13, 2005.

Tiseo et al, Epidermal growth factor receptor inhibitorsL a new prospective in the treatment of lung cancer, Curr. Med. Chem. Anti-Canc. Agents, 2004, pp. 139-148, vol. 4.

Hu et al., Discovery and validation of new molecular targets for ovarian cancer, Curr. Opin. Mol. Ther., 2003, pp. 625-630, vol. 5.

Kunkel et al., Inhibition of Glioma Angiogenesis and Growth in Vivo by Systemic Treatment with a Monoclonal Antibody against Vascular Endothelial Growth Factor Receptor-2[1] Cancer Research, Sep. 2001, pp. 6624-6628, vol. 61.

* cited by examiner

U.S. 7,973,017 B2

SEQUENCE LISTING

```
<160> NUMBER OF SEQ ID NOS: 53

<210> SEQ ID NO 1
<211> LENGTH: 2859
<212> TYPE: DNA
<213> ORGANISM: human

<400> SEQUENCE: 1
ctttccgcgg cattctttgg gcgtgagtca tgcaggtttg cagccagccc caaaggggt      60 gtgtgcgcga gcagagcgct ataaatacgg cgcctcccag tgcccacaac gcggcgtcgc    120
caggaggagc gcgcgggcac agggtgccgc tgaccgaggc gtgcaaagac tccagaattg    180
gaggcatgat gaagactctg ctgctgtttg tggggctgct gctgacctgg gagagtgggc    240
aggtcctggg ggaccagacg gtctcagaca atgagctcca ggaaatgtcc aatcagggaa    300
gtaagtacgt caataaggaa attcaaaatg ctgtcaacgg ggtgaaacag ataaagactc    360
tcatagaaaa aacaaacgaa gagcgcaaga cactgctcag caacctagaa gaagccaaga    420
agaagaaaga ggatgcccta aatgagacca gggaatcaga gacaaagctg aaggagctcc    480
caggagtgtg caatgagacc atgatggccc tctgggaaga gtgtaagccc tgcctgaaac    540
agacctgcat gaagttctac gcacgcgtct gcagaagtgg ctcaggcctg gttggccgcc    600
agcttgagga gttcctgaac cagagctcgc ccttctactt ctggatgaat ggtgaccgca    660
tcgactccct gctggagaac gaccggcagc agacgcacat gctggatgtc atgcaggacc    720
acttcagccg cgcgtccagc atcatagacg agctcttcca ggacaggttc ttcacccggg    780
agccccagga tacctaccac tacctgccct tcagcctgcc ccaccggagg cctcacttct    840
tctttcccaa gtcccgcatc gtccgcagct tgatgccctt ctctccgtac gagcccctga    900
acttccacgc catgttccag cccttccttg agatgataca cgaggctcag caggccatgg    960
acatccactt ccatagcccg gccttccagc acccgccaac agaattcata cgagaaggcg   1020
acgatgaccg gactgtgtgc cgggagatcc gccacaactc cacgggctgc ctgcggatga   1080
aggaccagtg tgacaagtgc cgggagatct tgtctgtgga ctgttccacc aacaacccct   1140
cccaggctaa gctgcggcgg gagctcgacg aatccctcca ggtcgctgag aggttgacca   1200
ggaaatacaa cgagctgcta aagtcctacc agtggaagat gctcaacacc tcctccttgc   1260
```

-continued

```
tggagcagct gaacgagcag tttaactggg tgtcccggct ggcaaacctc acgcaaggcg    1320
aagaccagta ctatctgcgg gtcaccacgg tggcttccca cacttctgac tcggacgttc    1380
cttccggtgt cactgaggtg gtcgtgaagc tctttgactc tgatcccatc actgtgacgg    1440
tccctgtaga agtctccagg aagaaccta aatttatgga gaccgtggcg gagaaagcgc    1500
tgcaggaata ccgcaaaaag caccgggagg agtgagatgt ggatgttgct tttgcaccta    1560
cgggggcatc tgagtccagc tccccccaag atgagctgca gccccccaga gagagctctg    1620
cacgtcacca agtaaccagg ccccagcctc caggccccca actccgccca gcctctcccc    1680
gctctggatc ctgcactcta acactcgact ctgctgctca tgggaagaac agaattgctc    1740
ctgcatgcaa ctaattcaat aaaactgtct tgtgagctga tcgcttggag ggtcctcttt    1800
ttatgttgag ttgctgcttc ccggcatgcc ttcattttgc tatgggggc aggcaggggg    1860 gatggaaaat aagtagaaac aaaaaagcag tggctaagat ggtataggga ctgtcatacc    1920
agtgaagaat aaaagggtga agaataaaag ggatatgatg acaaggttga tccacttcaa    1980
gaattgcttg ctttcaggaa gagagatgtg tttcaacaag ccaactaaaa tatattgctg    2040
caaatggaag ctttctgtt ctattataaa actgtcgatg tattctgacc aaggtgcgac     2100
aatctcctaa aggaatacac tgaaagttaa ggagaagaat cagtaagtgt aaggtgtact    2160
tggtattata atgcataatt gatgttttcg ttatgaaaac atttggtgcc cagaagtcca    2220
aattatcagt tttatttgta agagctattg cttttgcagc ggtttattt gtaaaagctg     2280 ttgatttcga gttgtaagag ctcagcatcc caggggcatc ttcttgactg tggcatttcc    2340
tgtccaccgc cggtttatat gatcttcata cctttccctg gaccacaggc gtttctcggc    2400
ttttagtctg aaccatagct gggctgcagt accctacgct gccagcaggt ggccatgact    2460
acccgtggta ccaatctcag tcttaaagct caggcttttc gttcattaac attctctgat    2520
agaattctgg tcatcagatg tactgcaatg gaacaaaact catctggctg catcccaggt    2580
gtgtagcaaa gtccacatgt aaatttatag cttagaatat tcttaagtca ctgtcccttg    2640
tctctctttg aagttataaa caacaaactt aaagcttagc ttatgtccaa ggtaagtatt    2700
ttagcatggc tgtcaaggaa attcagagta aagtcagtgt gattcactta atgatataca    2760
ttaattagaa ttatggggtc agaggtattt gcttaagtga tcataattgt aaagtatatg    2820
tcacattgtc acattaatgt caaaaaaaaa aaaaaaaa                           2859
```

```
<210> SEQ ID NO 2
<211> LENGTH: 21
<212> TYPE: DNA
<213> ORGANISM: human

<400> SEQUENCE: 2
gcacagcagg agaatcttca t                                              21

<210> SEQ ID NO 3
<211> LENGTH: 21
<212> TYPE: DNA
<213> ORGANISM: human

<400> SEQUENCE: 3
tggagtcttt gcacgcctcg g                                              21

<210> SEQ ID NO 4
<211> LENGTH: 21
<212> TYPE: DNA
<213> ORGANISM: human
```

```
<400> SEQUENCE: 4
cagcagcaga gtcttcatca t                                              21

<210> SEQ ID NO 5
<211> LENGTH: 21
<212> TYPE: DNA
<213> ORGANISM: human

<400> SEQUENCE: 5
attgtctgag accgtctggt c                                              21

<210> SEQ ID NO 6
<211> LENGTH: 21
<212> TYPE: DNA
<213> ORGANISM: human

<400> SEQUENCE: 6
ccttcagctt tgtctctgat t                                              21

<210> SEQ ID NO 7
<211> LENGTH: 21
<212> TYPE: DNA
<213> ORGANISM: human

<400> SEQUENCE: 7
agcagggagt cgatgcggtc a                                              21

<210> SEQ ID NO 8
<211> LENGTH: 21
<212> TYPE: DNA
<213> ORGANISM: human

<400> SEQUENCE: 8
atcaagctgc ggacgatgcg g                                              21

<210> SEQ ID NO 9
<211> LENGTH: 21
<212> TYPE: DNA
<213> ORGANISM: human

<400> SEQUENCE: 9
gcaggcagcc cgtggagttg t                                              21

<210> SEQ ID NO 10
<211> LENGTH: 21
<212> TYPE: DNA
<213> ORGANISM: human

<400> SEQUENCE: 10
ttcagctgct ccagcaagga g                                              21

<210> SEQ ID NO 11
<211> LENGTH: 21
<212> TYPE: DNA
<213> ORGANISM: human

<400> SEQUENCE: 11
aatttagggt tcttcctgga g                                              21

<210> SEQ ID NO 12
<211> LENGTH: 21
<212> TYPE: DNA
<213> ORGANISM: human
```

```
<400> SEQUENCE: 12
gctgggcgga gttgggggcc t                                              21

<210> SEQ ID NO 13
<211> LENGTH: 17
<212> TYPE: DNA
<213> ORGANISM: human

<400> SEQUENCE: 13
ggtgtagacg ccgcacg                                                   17

<210> SEQ ID NO 14
<211> LENGTH: 16
<212> TYPE: DNA
<213> ORGANISM: human

<400> SEQUENCE: 14
gcagcgcagc ccctgg                                                    16

<210> SEQ ID NO 15
<211> LENGTH: 22
<212> TYPE: DNA
<213> ORGANISM: human

<400> SEQUENCE: 15
gcagcagccg cagcccggct cc                                             22

<210> SEQ ID NO 16
<211> LENGTH: 18
<212> TYPE: DNA
<213> ORGANISM: human

<400> SEQUENCE: 16
agccgcagcc cggctcct                                                  18

<210> SEQ ID NO 17
<211> LENGTH: 20
<212> TYPE: DNA
<213> ORGANISM: human

<400> SEQUENCE: 17
cagcagccgc agcccggctc                                                20

<210> SEQ ID NO 18
<211> LENGTH: 20
<212> TYPE: DNA
<213> ORGANISM: human

<400> SEQUENCE: 18
gcagcagccg cagcccggct                                                20

<210> SEQ ID NO 19
<211> LENGTH: 20
<212> TYPE: DNA
<213> ORGANISM: human

<400> SEQUENCE: 19
agcagccgca gcccggctcc                                                20

<210> SEQ ID NO 20
<211> LENGTH: 21
<212> TYPE: DNA
<213> ORGANISM: artificial
```

```
<220> FEATURE:
<223> OTHER INFORMATION: mismatch primer

<400> SEQUENCE: 20
cagcagcaga gtatttatca t                                              21

<210> SEQ ID NO 21
<211> LENGTH: 21
<212> TYPE: DNA
<213> ORGANISM: human

<400> SEQUENCE: 21
guagaagggc gagcucuggt t                                              21

<210> SEQ ID NO 22
<211> LENGTH: 21
<212> TYPE: DNA
<213> ORGANISM: human

<400> SEQUENCE: 22
gaugcucaac accuccucct t                                              21

<210> SEQ ID NO 23
<211> LENGTH: 21
<212> TYPE: DNA
<213> ORGANISM: human

<400> SEQUENCE: 23
ggaggaggug uugagcauct t                                              21

<210> SEQ ID NO 24
<211> LENGTH: 21
<212> TYPE: DNA
<213> ORGANISM: human

<400> SEQUENCE: 24
cuaauucaau aaaacuguct t                                              21

<210> SEQ ID NO 25
<211> LENGTH: 21
<212> TYPE: DNA
<213> ORGANISM: human

<400> SEQUENCE: 25
gacaguuuua uugaauuagt t                                              21

<210> SEQ ID NO 26
<211> LENGTH: 19
<212> TYPE: DNA
<213> ORGANISM: human

<400> SEQUENCE: 26
uaauucaaca aaacugutt                                                 19

<210> SEQ ID NO 27
<211> LENGTH: 19
<212> TYPE: DNA
<213> ORGANISM: human

<400> SEQUENCE: 27
acaguuuugu ugaauuatt                                                 19

<210> SEQ ID NO 28
<211> LENGTH: 21
```

<212> TYPE: DNA
<213> ORGANISM: human

<400> SEQUENCE: 28
augaugaaga cucugcugct t          21

<210> SEQ ID NO 29
<211> LENGTH: 21
<212> TYPE: DNA
<213> ORGANISM: human

<400> SEQUENCE: 29
gcagcagagu cuucaucaut t          21

<210> SEQ ID NO 30
<211> LENGTH: 22
<212> TYPE: DNA
<213> ORGANISM: human

<400> SEQUENCE: 30
ugaaugaagg gacuaaccug tt          22

<210> SEQ ID NO 31
<211> LENGTH: 22
<212> TYPE: DNA
<213> ORGANISM: human

<400> SEQUENCE: 31
cagguuaguc ccuucauuca tt          22

<210> SEQ ID NO 32
<211> LENGTH: 22
<212> TYPE: DNA
<213> ORGANISM: human

<400> SEQUENCE: 32
cagaaauaga caaagugggg tt          22

<210> SEQ ID NO 33
<211> LENGTH: 22
<212> TYPE: DNA
<213> ORGANISM: human

<400> SEQUENCE: 33
ccccacuuug ucuauuucug tt          22

<210> SEQ ID NO 34
<211> LENGTH: 22
<212> TYPE: DNA
<213> ORGANISM: human

<400> SEQUENCE: 34
acagagacua agggaccaga tt          22

<210> SEQ ID NO 35
<211> LENGTH: 22
<212> TYPE: DNA
<213> ORGANISM: human

<400> SEQUENCE: 35
acagagacua agggaccaga tt          22

<210> SEQ ID NO 36
<211> LENGTH: 21

```
<212> TYPE: DNA
<213> ORGANISM: human

<400> SEQUENCE: 36
ccagagcucg cccuucuact t                                              21

<210> SEQ ID NO 37
<211> LENGTH: 21
<212> TYPE: DNA
<213> ORGANISM: human

<400> SEQUENCE: 37
guagaagggc gagcucuggt t                                              21

<210> SEQ ID NO 38
<211> LENGTH: 21
<212> TYPE: DNA
<213> ORGANISM: human

<400> SEQUENCE: 38
gucccgcauc guccgcagct t                                              21

<210> SEQ ID NO 39
<211> LENGTH: 21
<212> TYPE: DNA
<213> ORGANISM: human

<400> SEQUENCE: 39
gcugcggacg augcgggact t                                              21

<210> SEQ ID NO 40
<211> LENGTH: 21
<212> TYPE: DNA
<213> ORGANISM: human

<400> SEQUENCE: 40
cuaauucaau aaaacuguct t                                              21

<210> SEQ ID NO 41
<211> LENGTH: 21
<212> TYPE: DNA
<213> ORGANISM: human

<400> SEQUENCE: 41
gacaguuuua uugaauuagt t                                              21

<210> SEQ ID NO 42
<211> LENGTH: 19
<212> TYPE: DNA
<213> ORGANISM: human

<400> SEQUENCE: 42
augaugaaga cucugcugc                                                 19

<210> SEQ ID NO 43
<211> LENGTH: 19
<212> TYPE: DNA
<213> ORGANISM: human

<400> SEQUENCE: 43
gcagcagagu cuucaucau                                                 19

<210> SEQ ID NO 44
<211> LENGTH: 21
```

```
<212> TYPE: DNA
<213> ORGANISM: human

<400> SEQUENCE: 44
ccagagcucg cccuucuact t                                          21

<210> SEQ ID NO 45
<211> LENGTH: 17
<212> TYPE: DNA
<213> ORGANISM: human

<400> SEQUENCE: 45
ggtgtagacg ccgcacg                                               17

<210> SEQ ID NO 46
<211> LENGTH: 16
<212> TYPE: DNA
<213> ORGANISM: human

<400> SEQUENCE: 46
gcagcgcagc ccctgg                                                16

<210> SEQ ID NO 47
<211> LENGTH: 22
<212> TYPE: DNA
<213> ORGANISM: human

<400> SEQUENCE: 47
gcagcagccg cagcccggct cc                                         22

<210> SEQ ID NO 48
<211> LENGTH: 18
<212> TYPE: DNA
<213> ORGANISM: human

<400> SEQUENCE: 48
agccgcagcc cggctcct                                              18

<210> SEQ ID NO 49
<211> LENGTH: 20
<212> TYPE: DNA
<213> ORGANISM: human

<400> SEQUENCE: 49
cagcagccgc agcccggctc                                            20

<210> SEQ ID NO 50
<211> LENGTH: 20
<212> TYPE: DNA
<213> ORGANISM: human

<400> SEQUENCE: 50
gcagcagccg cagcccggct                                            20

<210> SEQ ID NO 51
<211> LENGTH: 20
<212> TYPE: DNA
<213> ORGANISM: human

<400> SEQUENCE: 51
agcagccgca gcccggctcc                                            20

<210> SEQ ID NO 52
<211> LENGTH: 1439
```

```
<212> TYPE: DNA
<213> ORGANISM: human

<400> SEQUENCE: 52
tgcggcggcg agggaggagg aagaagcgga ggaggcggct cccgcgctcg cagggccgtg      60
ccacctgccc gcccgcccgc tcgctcgctc gcccgccgcg ccgcgctgcc gaccgccagc     120
atgctgccga gagtgggctg ccccgcgctg ccgctgccgc cgccgccgct gctgccgctg     180
ctgccgctgc tgctgctgct actgggcgcg agtggcggcg gcggcggggc gcgcgcggag     240
gtgctgttcc gctgcccgcc ctgcacaccc gagcgcctgg ccgcctgcgg gcccccgccg     300
gttgcgccgc ccgccgcggt ggccgcagtg gccgaggcg cccgcatgcc atgcgcggag      360
ctcgtccggg agccgggctg cggctgctgc tcggtgtgcg cccggctgga gggcgaggcg     420
tgcggcgtct acaccccgcg ctgcggccag ggctgcgct gctatcccca cccgggctcc      480
gagctgcccc tgcaggcgct ggtcatgggc gagggcactt gtgagaagcg ccggacgcc      540
gagtatggcg ccagcccgga gcaggttgca gacaatggcg atgaccactc agaaggaggc     600
ctggtggaga accacgtgga cagcaccatg aacatgttgg gcgggggagg cagtgctggc     660
cggaagccc tcaagtcggg tatgaaggag ctggccgtgt tccgggagaa ggtcactgag      720
cagcaccggc agatgggcaa gggtggcaag catcaccttg gcctggagga gcccaagaag     780
ctgcgaccac cccctgccag gactcccctgc aacaggaac tggaccaggt cctggagcgg    840
atctccacca tgcgccttcc ggatgagcgg ggccctctgg agcacctcta ctccctgcac     900
atccccaact gtgacaagca tggcctgtac aacctcaaac agtgcaagat gtctctgaac     960
gggcagcgtg gggagtgctg gtgtgtgaac cccaacaccg gaagctgat ccagggagcc     1020
cccaccatcc gggggaccc cgagtgtcat ctcttctaca atgagcagca ggaggctcgc     1080
ggggtgcaca cccagcggat gcagtagacc gcagccagcc ggtgcctggc gccctgccc     1140
cccgcccctc tccaaacacc ggcagaaaac ggagagtgct tgggtggtgg gtgctggagg     1200
attttccagt tctgacacac gtatttatat ttggaaagag accagcaccg agctcggcac     1260
ctccccggcc tctctcttcc cagctgcaga tgccacacct gctccttctt gctttccccg     1320
ggggaggaag ggggttgtgg tcggggagct ggggtacagg tttggggagg gggaagagaa     1380
attttttattt ttgaaccccct gtgtcccttt tgcataagat taaaggaagg aaaagtaaa    1439

<210> SEQ ID NO 53
<211> LENGTH: 6316
<212> TYPE: DNA
<213> ORGANISM: human

<400> SEQUENCE: 53 tagtctctttt ggaaacttct gcaggggaaa agagctagga aagagctgca aagcagtgtg     60
ggcttttttcc cttttttgct ccttttcatt accctcctc cgttttcacc cttctccgga    120
cttcgcgtag aacctgcgaa tttcgaagag gaggtggcaa agtgggagaa aagaggtgtt    180
agggtttggg gttttttttgt ttttgttttt gttttttaat ttcttgattt caacattttc    240
tcccaccctc tcggctgcag ccaacgcctc ttacctgttc tgcggcgccg cgcaccgctg    300
gcagctgagg gttagaaagc ggggtgtatt ttagatttta agcaaaaatt ttaaagataa    360
atccattttt ctctcccacc cccaacgcca tctccactgc atccgatctc attatttcgg    420
tggttgcttg ggggtgaaca attttgtggc ttttttttccc ctataattct gacccgctca   480
ggcttgaggg tttctccggc ctccgctcac tgcgtgcacc tggcgctgcc ctgcttcccc    540
caacctgttg caaggcttta attcttgcaa ctgggacctg ctcgcaggca ccccagccct    600
```

```
ccacctctct ctacattttt gcaagtgtct gggggagggc acctgctcta cctgccagaa    660
attttaaaac aaaaacaaaa acaaaaaaat ctccggggc cctcttggcc cctttatccc     720
tgcactctcg ctctcctgcc ccaccccgag gtaaagggg cgactaagag aagatggtgt     780
tgctcaccgc ggtcctcctg ctgctggccg cctatgcggg gccggcccag agcctgggct    840
ccttcgtgca ctgcgagccc tgcgacgaga agccctctc catgtgcccc ccagccccc      900
tgggctgcga gctggtcaag gagccgggct gcggctgctg catgacctgc gccctggccg    960
aggggcagtc gtgcggcgtc tacaccgagc gctgcgccca ggggctgcgc tgcctccccc   1020
ggcaggacga ggagaagccg ctgcacgccc tgctgcacgg ccgcggggtt tgcctcaacg   1080
aaaagagcta ccgcgagcaa gtcaagatcg agagagactc ccgtgagcac gaggagccca   1140
ccacctctga gatggccgag gagacctact cccccaagat cttccggccc aaacacaccc   1200
gcatctccga gctgaaggct gaagcagtga agaaggaccg cagaaagaag ctgacccagt   1260
ccaagtttgt cggggagcc gagaacactg cccacccccg gatcatctct gcacctgaga    1320
tgagacagga gtctgagcag ggcccctgcc gcagacacat ggaggcttcc ctgcaggagc   1380
tcaaagccag cccacgcatg gtgccccgtg ctgtgtacct gcccaattgt gaccgcaaag   1440
gattctacaa gagaaagcag tgcaaacctt cccgtggccg caaacgtggc atctgctggt   1500
gcgtggacaa gtacgggatg aagctgccag gcatggagta cgttgacggg gactttcagt   1560
gccacacctt cgacagcagc aacgttgagt gatgcgtccc cccccaacct ttccctcacc   1620
ccctcccacc cccagcccg actccagcca gcgcctccct ccaccccagg acgccactca    1680
tttcatctca tttaagggaa aaatatatat ctatctattt gaggaaactg aggacctcgg   1740
aatctctagc aagggctcaa cttcgaaaat ggcaacaaca gagatgcaaa aagctaaaaa   1800
gacaccccc ccctttaaat ggttttcttt ttgaggcaag ttggatgaac agagaaggga    1860
agagaggaag aacgagagga agagaaggga aggaagtgtt tgtgtagaag agagagaaag   1920
acgaatagag ttaggaaaag gaagacaagc aggtgggcag gaaggacatg caccgagacc   1980
aggcaggggc ccaactttca cgtccagccc tggcctgggg tcgggagagg tgggcgctag   2040
aagatgcagc ccaggatgtg gcaatcaatg acactattgg ggtttcccag gatggattgg   2100
tcaggggggag aaaggaaaag gcaaaacact ccaggacctc tcccggatct gtctcctcct  2160
ctagccagca gtatggacag ctggaccct gaacttcctc tcctcttacc tgggcagagt    2220
gttgtctctc cccaaatttta taaaaactaa aatgcattcc attcctctga agcaaaaca   2280
aattcataat tgagtgatat taaatagaga ggttttcgga agcagatctg tgaatatgaa   2340
atacatgtgc atatttcatt ccccaggcag acatttttta gaaatcaata catgccccaa   2400
tattggaaag acttgttctt ccacggtgac tacagtacat gctgaagcgt gccgtttcag   2460
ccctcattta attcaatttg taagtagcgc agcagcctct gtggggagg ataggctgaa    2520
aaaaaaagt gggctcgtat ttatctacag gactccatat agtcatatat aggcatataa    2580
atctattctt tttctttgtt ttttctttc ttcctttctt tcaaaggttt gcattaactt    2640
ttcaaagtag ttcctatagg ggcattgagg agcttcctca ttctgggaaa actgagaaaa   2700
cccatattct cctaatacaa cccgtaatag cattttttgcc tgcctcgagg cagagtttcc  2760
cgtgagcaat aaactcagct ttttttgtggg gcacagtact ggatttgaca gtgattccc   2820
acgtgtgttc atctgcaccc accgagccag gcagaggcca gcctccgtg gtgcacacag    2880
cacgcgcctc agtccatccc attttagtct ttaaaccctc aggaagtcac agtctccgga   2940
caccacacca catgagccca acaggtccac gatggatcca ccagtcccac cccagccttt   3000
```

```
tcctttcatc tgaacagaat gtgcattttt ggaagcctcc ctcactctcc atgctggcag    3060
agcaggaggg agactgaagt aagagatggc agagggagat ggtggcaaaa aggtttagat    3120
gcaggagaac agtaagatgg atggttccgg ccagagtcga tgtggggagg aacagagggc    3180
tgaagggaga gggggctgac tgttccattc tagctttggc acaaagcagc agaaaggggg    3240
aaaagccaat agaaatttcc ttagcttccc caccatatgt attttctagg atttgagagg    3300
aaagagagga aaatggggga atgggttgca aaatagaaat gagcttaatc caggccgcag    3360
agccagggaa ggtgagtaac tttaggaggg tgctagactt tagaagccag ataggaagaa    3420
tcagtctaaa ctggccatgc tttggaaggg acaagactat gtgctccgct gcccaccttc    3480
agcctgcaat gagggactga ggcccacgag tctttccagc tcttcctcca ttctggccag    3540
tccctgcatc ctccctgggg tggaggatgg aaggaaagct gggacaagca gggaacgcat    3600
gattcaggga tgctgtcact cggcagccag attccgaaac tcccattctc caatgacttc    3660
ctcaaccaat gggtggcctt gtgactgttc tttaaggctg aagatatcca ggaaggggg    3720 cttggacact ggccaaggag acccttcgt gctgtggaca cagctctctt cactctttgc    3780
tcatggcatg acacagcgga gaccgcctcc aacaacgaat tgggggctac gaagaggaat    3840
agcgaaaaag caaatctgtt tcaactgatg ggaaccctat agctatagaa cttgggggct    3900
atctcctatg cccctggaca ggacagttgg ctggggacag gagaagtgct caatcttcat    3960
gagacaaagg ggcccgatag ggccagcagc cacaaggcct tgacctgccg agtcagcatg    4020
ccccatctct ctgcacagct gtcccctaaa cccaactcac gtttctgtat gtcttaggcc    4080
agtatcccaa acctcttcca cgtcactgtt cttccaccc attctccctt tgcatcttga    4140
gcagttatcc aactaggatc tgccaagtgg atactgggt gccactcccc tgagaaaaga    4200
ctgagccagg aactacaagc tcccccaca ttcctcccag cctggaccta attcttgaga    4260
ggggctctct cttcacggac tgtgtctgga ctttgagcag gcttctgccc cttgcgttgg    4320
ctctttgctg ccagccatca ggtggggat tagagcctgg tgtaagtgcg ccagactctt    4380
ccggtttcca aagttcgtgc ctgcgaaccc aaacctgtga gtctcttctg catgcaggag    4440
tttctcctgg gcagctggtc actccccaga gaagctgggc cttcatggac acatggaact    4500
aagcctccca aatgggagtt ctggctgagc ccagggtggg gagatcctgg gaagggaggc    4560
actggaggaa gacggcacct cttcccccat ggcagggtgt gagggaggca ggtttggaat    4620
ggtgcgagta tggcaatcta agcaggggtc tggtctcttt gactccaggc tggccttgg    4680 ccgactgtct gctcacccag agaccttgga ctccggacta ccatggctc cgaatctaag    4740 tgctgcccac tccatgctc acacccacag aaggtcttcc catcccctt agattcgtgc    4800 ctcactccac cagtgaggaa gatgcctctg tctttcccac gactgccagg agatagggaa    4860
gcccagccag gactgaccct ccttcctcca gcctgccctg acccacctgg caaagcaggg    4920
cacatgggga ggaagagact ggaacctttc tttgacagcc aggcctagac agacaggcct    4980
ggggacactg gccccatgag gggaggaagg caggcgcacg aggtccaggg aggccctttt    5040
ctgatcatgc cccttctctc ccaccccatc tccccaccac cacctctgtg gcctccatgg    5100
tacccccaca gggctggcct ccctagagg gtgggcctca accacctgct cccgccacgc    5160
accggttagt gagacagggc tgccacggca accgccaagc cccctcaag gtgggacagt    5220 accccggacc catccactca ctcctgagag ggctccggcc cagaatggga acctcagaga    5280
agagctctaa ggagaagaaa ccccatacg tcagagagga tatgtctggc ttccaagaga    5340
aaggaggctc cgttttgcaa agtggaggag ggacgaggga caggggtttc accagccagc    5400
```

```
aacctgggcc ttgtactgtc tgtgtttta aaaccactaa agtgcaagaa ttacattgca    5460
ctgtttctcc acttttatt ttctcttagg cttttgtttc tatttcaaac atactttctt    5520
ggttttctaa tggagtatat agtttagtca tttcacagac tctggcctcc tctcctgaaa    5580
tccttttgga tggggaaagg gaaggtgggg agggtccgag gggaagggga ccccagcttc    5640
cctgtgcccg ctcaccccac tccaccagtc cccggtcgcc agccggagtc tcctctctac    5700
cgccactgtc acaccgtagc ccacatggat agcacagttg tcagacaaga ttccttcaga    5760
ttccgagttg cctaccggtt gttttcgttg ttgttgttgt tgtttttctt tttctttttt    5820
tttttgaaga cagcaataac cacagtacat attactgtag ttctctatag ttttacatac    5880
attcatacca taactctgtt ctctcctctt ttttgttttc aactttaaaa acaaaaataa    5940
acgatgataa tctttactgg tgaaaaggat ggaaaaataa atcaacaaat gcaaccagtt    6000
tgtgagaaaa aaaaaaaaaa gccgaaaaaa aaaaaaaaaa cacctgaatg cggaagagct    6060
cggctcccgt ttagcatttt gtacttaagg aaataaaaaa ccaacaaagg atctcacatt    6120
ttcttaaaaa gtgaagattg ctgtatacta tttattcaac ttataattta tgttactcct    6180
tgatctttgt cttttgtcat gacaaagcat ttatttaata aagttatgca ttcagttaaa    6240
aaaaaaaaaa aaaaaaaaaa aaaaaaaaaa aaaaaaaaa aaaaaaaaaa aaaaaaaaaa    6300
aaaaaaaaaa aaaaaa                                                   6316
```

TREATMENT OF CANCER BY INHIBITION OF IGFBP'S AND CLUSTERIN

This application is continuation-in-part of U.S. patent application Ser. No. 10/346,493, filed Jan. 17, 2003, which claims the benefit of U.S. Provisional Application No. 60/350,046 filed Jan. 17, 2002. This application also claims the benefit of U.S. Provisional Applications 60/522,948 filed Nov. 23, 2004 and 60/522,960 filed Nov. 24, 2004. All of these applications are incorporated herein by reference.

FIELD OF THE INVENTION

The present application relates to a method for treating cancer in a mammalian subject using a combination of therapeutic agents, one of which is an oligonucleotide effective to reduce the amount of clusterin, also known as testosterone-repressed prostate message-2 (TRPM-2) in the cancer cells, and the other of which reduces expression of insulin-like growth factor binding protein 2 (IGFBP-2) and/or insulin-like growth factor binding protein 5 (IGFBP-5), and also stimulates the expression of clusterin as a consequence of its action on the target. By way of non-limiting example, the agent that reduces IGFBP-2 and/or IGFBP-5 may be a bispecific antisense that inhibits IGFBP-2 and IGFBP-5 expression.

BACKGROUND OF THE INVENTION

After lung cancer, breast cancer is the second leading cause of cancer deaths in women. According to the World Health Organization, more than 1.2 million people will be diagnosed with breast cancer this year worldwide, and The American Cancer Society estimates that in 2004, over 200,000 women in the United States will be diagnosed with invasive breast cancer (Stages I-IV), and about 40,000 women and almost 500 men will die from breast cancer in the United States in 2004.

Prostate cancer is the most common cancer that affects men, and the second leading cause of cancer deaths in men in the Western world. Because prostate cancer is an androgen-sensitive tumor, androgen withdrawal, for example via castration, is utilized in some therapeutic regimens for patients with advanced prostate cancer. Androgen withdrawal leads to extensive apoptosis in the prostate tumor, and hence to a regression of the disease. However, castration-induced apoptosis is not complete, and a progression of surviving tumor cells to androgen-independence ultimately occurs. This progression is the main obstacle to improving survival and quality of life, and efforts have therefore been made to target androgen-independent cells. These efforts have focused on non-hormonal therapies targeted against androgen-independent tumor cells, however as of a 1998 report, no non-hormonal agent had improved survival. Oh et al., J. Urol 160: 1220-1229 (1998) Alternative approaches are therefore indicated.

Ovarian cancer is the seventh most common cancer and the fourth leading cause of death after lung and bronchus, breast, and colorectal cancers among U.S. women. A woman's risk of getting ovarian cancer during her lifetime is about 1 in 58. The risk of getting this cancer and dying from it is 1 in 98.

Colorectal cancer, a diagnosis which comprises both cancer of the colon and the associated rectal region, is the second leading cause of cancer death in the U.S.

Standard treatments for these various cancers include surgery, radiation, chemotherapy and hormonal therapies. Each of these treatments has drawbacks including surgical risks, illness and loss of productivity associated with radiation or chemotherapy, reproductive and hormonal side effects, and unreliable survival rates.

Thus cancer is a serious disease, fatal in many cases, and requires improved treatments to reduce fatalities and prevalence.

Clusterin or "TRPM-2" is a ubiquitous protein, with a diverse range of proposed activities. In prostate epithelial cells, expression of clusterin increases immediately following castration, reaching peak levels in rat prostate cells at 3 to 4 days post castration, coincident with the onset of massive cell death. These results have led some researchers to the conclusion that clusterin is a marker for cell death, and a promoter of apoptosis. On the other hand, Sertoli cells and some epithelial cells express high levels of clusterin without increased levels of cell death. Sensibar et al., (1995) [1] reported on in vitro experiments performed to more clearly elucidate the role of clusterin in prostatic cell death. The authors used LNCaP cells transfected with a gene encoding clusterin, and observed whether expression of this protein altered the effects of tumor necrosis factor α (TNFα), to which LNCaP cells are very sensitive. Treatment of the transfected LNCaP cells with TNFα resulted in a transient increase in clusterin levels for a few hours, but these levels had dropped by the time DNA fragmentation preceding cell death was observed.

United States published patent application US 20030166591 discloses the use of antisense therapy which reduces the expression of clusterin for the treatment of cancer of prostate and renal cell cancer.

U.S. Pat. No. 6,383,808 discloses compositions, particularly oligonucleotides, and methods for modulating the expression of clusterin.

United States published patent application 2004096882 discloses RNAi therapeutic probes targeting cancer associated proteins including clusterin.

United States published patent application US2004053874 discloses antisense modulation of clusterin expression.

United States published patent application US 2003166591 discloses cluserin antisense therapy using an oligonucleotide having 2'-O-(2-methoxy)ethyl modifications.

United States published patent application US 2003158130 discloses the use of chemotherapy-sensitization and radiation-sensitization of cancer by antisense clusterin oligodeoxynucleotides.

SUMMARY OF THE INVENTION

Applicants have found that agents that reduce the amount of IGFBP-2 and/or IGFBP-5 and that are known to be useful in the treatment of cancer result in increased expression of the protein clusterin. Since clusterin can provide protection against apoptosis, this secondary effect detracts from the efficacy of the therapeutic agent. In overcoming this, the present invention provides a combination of therapeutic agents that is useful in the treatment of cancer. The combination comprises an agent that reduces the amount of IGFBP-2 and/or IGFBP-5 and that stimulates expression of clusterin as a secondary effect, and an oligonucleotide that is effective to reduce the amount of clusterin in cancer cells. In some embodiments of the invention, the agent that reduces IGFBP-2 and/or IGFBP-5 is a bispecific antisense species. The oligonucleotide may be an antisense oligonucleotide or an RNAi oligonucleotide.

The combination of the invention is useful in a method for treating cancer in a mammalian subject, comprising administering to the subject the agent that reduces IGFBP-2 and/or IGFBP-5 and an oligonucleotide effective to reduce the amount of clusterin in the cancer cells.

The cancer may be breast cancer, osteosarcoma, lung cancer, pancreatic cancer, salivary gland cancer, colon cancer, prostate cancer, endometrial cancer, and bladder, for example.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention.

DETAILED DESCRIPTION OF THE INVENTION

Definitions

Definition and Sequences for IGFBP 2/5

Figure 1A:
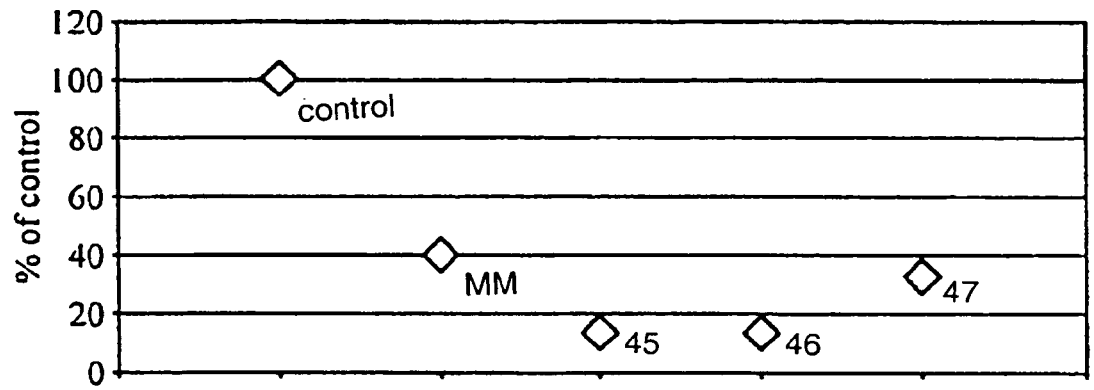
FIG. 1 the amount of IGFBP-2 and IGFBP-5 expression observed in LNCaP and PC3 cells, respectively, upon administration of one of three bispecific antisense oligonucleotides, a mismatch control (MM), or no olignucleotide (control).

As used in the specification and claims of this application, the terms "insulin-dependent growth factor-2" and "IGFBP-2" are used interchangeably. The nucleotide sequence of human IGFBP-2 is known from NCBI sequence accession no. NM_000597 and is set forth in Seq. ID No. 52.

As used in the specification and claims of this application, the terms "insulin-dependent growth factor-5" and "IGFBP-5" are used interchangeably. The nucleotide sequence of human IGFBP-2 is known from NCBI sequence accession no. NM_000599 and is set forth in Seq. ID No. 53.

As used in the specification and claims of this application, the term "clusterin" refers to the glycoprotein originally derived from ram rete testes, and to homologous proteins derived from other mammalian species, including humans, whether denominated as clusterin or an alternative name. The sequences of numerous clusterin species are known. For example, the sequence of human clusterin is reported by Wong et al., (1994) [2], and in NCBI sequence accession number NM_001831 and is set forth in Seq. ID No.: 1. In this sequence, the coding sequence spans bases 48 to 1397.

As used in this application, the term "amount of clusterin" refers to the amount of clusterin which is present in a form which is functional to provide anti-apoptotic protection. The effective amount of clusterin may be reduced through restricting production of clusterin (at the transcription or translation level) or by degrading clusterin at a rate faster than it is being produced. Further, it will be appreciated that inhibition occurs when the clusterin would otherwise be present if the antisense oligonucleotide had not been administered.

As used in this application, the term "amount of IGFBP-2 and/or IGFBP-5" refers to the amount of the binding protein which is present.

As used in the specification, "antisense oligonucleotide" refers to stretches of single-stranded DNA, usually chemically modified, whose sequence (3'→5') is complementary to the sense sequence of a molecule of mRNA. Antisense molecules thereby effectively inhibit gene expression by forming RNA/DNA duplexes, and offer a more targeted option for cancer therapy than chemotherapy or radiation. Antisense is believed work by a variety of mechanisms, including physically blocking the ability of ribosomes to move along the messenger RNA, and hastening the rate at which the mRNA is degraded within the cytosol. The abbreviation ASO may also be used to refer to an antisense oligonucleotide As used in the specification and claims of this application, the term "combination" refers to an assemblage of reagents for use in therapy either by simultaneous or contemporaneous administration. Simultaneous administration refers to administration of an admixture (whether a true mixture, a suspension, an emulsion or other physical combination) of the agent that reduces IGFBP-2 and/or IGFBP-5 and the oligonucleotide. In this case, the combination may be the admixture or separate containers of the agent and the oligonucleotide that are combined just prior to administration. Contemporaneous administration refers to the separate administration of the agent and the oligonucleotide at the same time, or at times sufficiently close together that a enhanced or synergistic activity relative to the activity of either the agent or the oligonucleotide alone is observed. In this, the combination comprises separate containers of the agent and the oligonucleotide Agents That Reduce IGFBP-2 and/or IGFBP-5

The agent used in the combinations and method of the present invention is one that reduced the amount of IGFBP-2 and/or IGFBP-5.

In one embodiment of the invention, this agent is a bispecific agent complementary to portions of the IGFBP-2 and/or IGFBP-5 gene or mRNA, wherein substantially all of the oligodeoxynucleotide consists essentially of a sequence of bases that is complementary to a portion of portions of a gene encoding human IGFBP-2 and substantially all of the oligodeoxynucleotide is also complementary to a gene encoding human IGFBP-5, and wherein the oligodeoxynucleotide which is of sufficient length (in general at least 15 bases) to act as an antisense inhibitor of the effective amount of human IGFBP-2 and human IGFBP-5. Specific bispecific antisense oligonucleotides of this type that can be used as the agent in the invention consist essentially of a series of bases as set forth in Seq. ID. No. 45 through 51 as follows:

| | |
|---|---|
| ggtgtagacgccgcacg | Seq ID No.: 45 |
| gcagcgcagccctgg | Seq ID No.: 46 |
| gcagcagccgcagcccggctcc | Seq ID No.: 47 |
| agccgcagcccggctcct | Seq ID No.: 48 |
| cagcagccgcagcccggctc | Seq ID No.: 49 |
| gcagcagccgcagcccggct | Seq ID No.: 50 |
| agcagccgcagcccggctcc | Seq ID No.: 51 |

These antisense oligonucleotides employed may be modified to increase the stability of the antisense oligonucleotide in vivo. For example, the antisense oligonucleotides may be employed as phosphorothioate derivatives (replacement of a non-bridging phosphoryl oxygen atom with a sulfur atom) which have increased resistance to nuclease digestion. Increased antisense oligonucleotide stability can also be achieved using molecules with 2-methoxyethyl (MOE) substituted backbones as described generally in U.S. Pat. No. 6,451,991 and U.S. patent application Ser. No. 10/080,794 which are incorporated herein by reference.

Reduction in the amount of IGFBP-2 and/or IGFBP-5 can be accomplished using therapeutics, alone or in combination, that target the two binding proteins individually. By way of non-limiting example, antisense species that reduce IGFBP-2 or IGFBP-5 individually are described in International Patent Publication Nos. WO02/22642 and WO01/05435, which are incorporated herein by reference. Antisense sequences are also disclosed in Huynh, Hung, et al.; "A Role for Insulin-Like Growth Factor Binding Protein 5 in the Antiproliferative Action of the Antiestrogen ICI 182782"; Cell Growth & Differentiation, Vol. 7, No. 11, pages 1501-1506; 1996.

The amount of antisense oligonucleotide administered is one effective to reduce the effective amount of levels of IGFBP-2 and/or IGFBP-5 in the tumor/cancer cell of concern. As noted above, in the context of the present invention, applicants do not intend to be bound by any specific mechanism by which this reduction may occur, although it is noted that the reduction may occur as a result of reduced expression of IGFBP-2 and -5 if the antisense molecule interferes with translation of the mRNA, or via an RNase mediated mechanism. Furthermore, it will be appreciated that the appropriate therapeutic amount will vary both with the effectiveness of the specific antisense oligonucleotide employed, and with the nature of any carrier used. The determination of appropriate amounts for any given composition is within the skill in the art, through standard series of tests designed to assess appropriate therapeutic levels The combination and method of the invention can also be practiced using siRNA molecules to reduce IGFBP and/or IGFBP-5. By way of non-limiting example, antisense species that reduce IGFBP-2 or IGFBP-5 individually are described in International Patent Publication No. WO2004/018676, which is incorporated herein by reference.

Reduction in the amount of IGFBP-2 and/or 5 may also be obtained using a fusion protein that contains distinct regions that target the two proteins. By way of non-limiting example, such a fusion protein is disclosed in U.S. Pat. No. 5,929,040, which is incorporated herein by reference.

Other molecules that can be used to reduce the amount of IGFBP-2 and/or IGFBP-5 include therapeutic antibodies such as those described in International Patent Publication No. WO00/69454.

Oligonucleotides

Antisense Oligonucleotides (ASO) Antisense oligonucleotides are synthetic polymers made up of monomers of deoxynucleotides like those in DNA. In the present application, the term antisense oligonucleotides includes antisense oligodeoxynucleotides.

The antisense oligonucleotides for use in the combination and method of the invention for treatment of cancer in humans may be complementary to the nucleotide sequence of human clusterin as set forth in Seq. ID No. 1. Exemplary sequences which can be employed as antisense oligonucleotides in the combination and method of the invention are disclosed in PCT Patent Publication WO 00/49937, US Patent Publication US-2002-0128220-A1, and U.S. Pat. No. 6,383,808, all of which are incorporated herein by reference in those jurisdictions where such incorporation is permitted. In specific embodiments, the antisense oligonucleotide may span either the translation initiation site or the termination site of clusterin. The antisense oligonucleotide comprises and may consist essentially of an oligonucleotide selected from the group consisting of Seq. ID. Nos.: 2 to 19 as shown in Table 1, or more specifically Seq. ID. No. 4, Seq. ID. No. 5 and Seq. ID. No. 12.

TABLE 1

| Seq ID No. | Description | SEQUENCE (5' to 3') |
|---|---|---|
| 2 | Antisense TRPM-2 oligonucleotide | GCACAGCAGGAGAATCTTCAT |
| 3 | Antisense TRPM-2 oligonucleotide | TGGAGTCTTTGCACGCCTCGG |
| 4 | Antisense oligonucleotide corresponding to the human TRPM-2 translation initiation site | CAGCAGCAGAGTCTTCATCAT |
| 5 | Antisense TRPM-2 oligonucleotide | ATTGTCTGAGACCGTCTGGTC |
| 6 | Antisense TRPM-2 oligonucleotide | CCTTCAGCTTTGTCTCTGATT |
| 7 | Antisense TRPM-2 oligonucleotide | AGCAGGGAGTCGATGCGGTCA |
| 8 | Antisense TRPM-2 oligonucleotide | ATCAAGCTGCGGACGATGCGG |
| 9 | Antisense TRPM-2 oligonucleotide | GCAGGCAGCCCGTGGAGTTGT |
| 10 | Antisense TRPM-2 oligonucleotide | TTCAGCTGCTCCAGCAAGGAG |
| 11 | Antisense TRPM-2 oligonucleotide | AATTTAGGGTTCTTCCTGGAG |
| 12 | Antisense TRPM-2 oligonucleotide | GCTGGGCGGAGTTGGGGCCT |
| 13 | Antisense TRPM-2 oligonucleotide | GGTGTAGACG CCGCACG |
| 14 | Antisense TRPM-2 oligonucleotide | GCAGCGCAGC CCCTGG |
| 15 | Antisense TRPM-2 oligonucleotide | GCAGCAGCCG CAGCCCGGCT CC |
| 16 | Antisense TRPM-2 oligonucleotide | AGCCGCAGCC CGGCTCCT |
| 17 | Antisense TRPM-2 oligonucleotide | CAGCAGCCGC AGCCCGGCTC |
| 18 | Antisense TRPM-2 oligonucleotide | GCAGCAGCCG CAGCCCGGCT |
| 19 | Antisense TRPM-2 oligonucleotide | AGCAGCCGCAGCCCGGCTCC |
| 20 | 2 base TRPM-2 mismatch oligonucleotide used as a control | CAGCAGCAGAGTATTTATCAT |

As used in the specification and claims of this application, the phrase "consist essentially of" means that the oligonucleotide contains just the based of the identified sequence or such bases and a small number of additional bases that do not materially alter the antisense function of the oligonucleotide.

In order avoid digestion by DNAse, antisense oligonucleotides and ODNs are often chemically modified. For example, phosphorothioate oligodeoxynucleotides are stabilized to resist nuclease digestion by substituting one of the non-bridging phosphoryl oxygen of DNA with a sulfur. Increased antisense oligonucleotide stability can also be achieved using molecules with 2-methoxyethyl (MOE) substituted backbones as described generally in U.S. Pat. No. 6,451,991, incorporated by reference in those jurisdictions allowing such incorporation, and US Published patent application US-2003-0158143-A1. Thus, in the combination and method of the invention, the antisense oligonucleotide be modified to enhance in vivo stability relative to an unmodified oligonucleotide of the same sequence. The modification may be a (2'-O-(2-methoxyethyl) modification. The oligonucleotide may have a phosphorothioate backbone throughout, the sugar moieties of nucleotides 1-4 and 18-21 may bear 2'-O-methoxyethyl modifications and the remaining nucleotides may be 2'-deoxynucleotides.

The antisense oligonucleotide may be a 5-10-5 gap-mer methoxyl ethyl modified (MOE) oligonucleotide corresponding to SEQ ID NO.:5 below. The antisense oligonucleotide may be from 10-25 bases in length, or from 15-23 bases in length, or from 18-22 bases in length, or 21 bases in length. A particularly preferred antisense oligonucleotide is a 21 mer oligonucleotide (CAGCAGCAGAGTCTTCATCAT; SEQ ID NO.: 4) targeted to the translation initiation codon and next 6 codons of the human clusterin sequence with a 2'-MOE modification. In one embodiment, this oligonucleotide has a phosphorothioate backbone throughout. The sugar moieties of nucleotides 1-4 and 18-21 (the "wings") bear 2'-O-methoxyethyl modifications and the remaining nucleotides (nucleotides 5-17; the "deoxy gap") are 2'-deoxynucleotides. Cytosines in the wings (i.e., nucleotides 1, 4 and 19) are 5-methylcytosines.

RNAi Oligonucleotides

Reduction in the amount of clusterin may also be achieved using RNA interference or "RNAi". RNAi is a term initially coined by Fire and co-workers to describe the observation that double-stranded RNA (dsRNA) can block gene expression [3]. Double stranded RNA, or dsRNA directs gene-specific, post-transcriptional silencing in many organisms, including vertebrates. RNAi involves mRNA degradation, but many of the biochemical mechanisms underlying this interference are unknown. The use of RNAi has been further described [3,4].

The initial agent for RNAi is a double stranded RNA molecule corresponding to a target nucleic acid. The dsRNA is then thought to be cleaved in vivo into short interfering RNAs (siRNAs) which are 21-23 nucleotides in length (19-21 bp duplexes, each with 2 nucleotide 3' overhangs). Alternatively, RNAi may be effected via directly introducing into the cell, or generating within the cell by introducing into the cell a suitable precursor (e.g. vector, etc.) of such an siRNA or siRNA-like molecule. An siRNA may then associate with other intracellular components to form an RNA-induced silencing complex (RISC).

RNA molecules used in embodiments of the present invention generally comprise an RNA portion and some additional portion, for example a deoxyribonucleotide portion. The total number of nucleotides in the RNA molecule is suitably less than 49 in order to be effective mediators of RNAi. In preferred RNA molecules, the number of nucleotides is 16 to 29, more preferably 18 to 23, and most preferably 21-23.

In certain embodiments of the invention, the siRNA or siRNA-like molecule is less than about 30 nucleotides in length. In a further embodiment, the siRNA or siRNA-like molecules are about 21-23 nucleotides in length. In an embodiment, siRNA or siRNA-like molecules comprise and 19-21 bp duplex portion, each strand having a 2 nucleotide 3' overhang.

In certain embodiments of the invention, the siRNA or siRNA-like molecule is substantially identical to a clusterin-encoding nucleic acid or a fragment or variant (or a fragment of a variant) thereof. Such a variant is capable of encoding a protein having clusterin-like activity. In some embodiments, the sense strand of the siRNA or siRNA-like molecule is targeted to the same portion of the DNA as antisense SEQ ID NO: 4 or a fragment thereof (RNA having U in place of T residues of the DNA sequence). In other embodiments, the RNAi sequence consists of Seq. Id. No. 41 or 43. For example, United States published patent application 2004096882 discloses RNAi therapeutic probes targeting clusterin. In addition, reagents and kits for performing RNAi are available commercially from for example Ambion Inc. (Austin, Tex., USA) and New England Biolabs Inc. (Beverly, Mass., USA). Suitable sequences for use as RNAi in the present invention are set forth in the present application as Seq. ID Nos. 21 to 44 as shown in Table 2.

TABLE 2

| SEQ ID No. | Description | SEQUENCE |
|---|---|---|
| 21 | RNAi for human clusterin | GUAGAAGGGC GAGCUCUGGTT |
| 22 | RNAi for human clusterin | GAUGCUCAACACCUCCUCCT T |
| 23 | RNAi for human clusterin | GGAGGAGGUG UUGAGCAUCT T |
| 24 | RNAi for human clusterin | CUAAUUCAAU AAAACUGUCT T |
| 25 | RNAi for human clusterin | GACAGUUUUA UUGAAUUAGT T |
| 26 | RNAi for human clusterin | UAAUUCAACA AAACUGUTT |
| 27 | RNAi for human clusterin | ACAGUUUUGU UGAAUUAUU |
| 28 | RNAi for human clusterin | AUGAUGAAGA CUCUGCUGCT T |
| 29 | RNAi for human clusterin | GCAGCAGAGU CUUCAUCAUT T |
| 30 | RNAi for human clusterin | UGAAUGAAGG GACUAACCUG TT |
| 31 | RNAi for human clusterin | CAGGUUAGUC CCUUCAUUCA TT |
| 32 | RNAi for human clusterin | CAGAAAUAGA CAAAGUGGGG TT |
| 33 | RNAI for human clusterin | CCCCACUUUG UCUAUUUCUG TT |
| 34 | RNAi for human clusterin | ACAGAGACUA AGGGACCAGA TT |
| 35 | RNAi for human clusterin | ACAGAGACUA AGGGACCAGA TT |
| 36 | RNAi for human clusterin | CCAGAGCUCG CCCUUCUACT T |

TABLE 2-continued

| SEQ ID No. | Description | SEQUENCE |
|---|---|---|
| 37 | RNAi for human clusterin | GUAGAAGGGC GAGCUCUGGT T |
| 38 | RNAi for human clusterin | GUCCCGCAUC GUCCGCAGCT T |
| 39 | RNAi for human clusterin | GCUGCGGACG AUGCGGGACT T |
| 40 | RNAi for human clusterin | CUAAUUCAAU AAAACUGUCT T |
| 41 | RNAI for human clusterin | GACAGUUUUA UUGAAUUAGT T |
| 42 | RNAi for human clusterin | AUGAUGAAGA CUCUGCUGC |
| 43 | RNAi for human clusterin | GCAGCAGAGU CUUCAUCAU |
| 44 | RNAI for human clusterin | CCAGAGCUCG CCCUUCUACT T |

Cancers That Can Be Treated

The combination of the present application is useful in the treatment of a variety of cancers for which IGFBP-2 and/or IGFBP-5 is considered relevant. Such cancers include without limitation endocrine-regulated tumors, for example, breast, prostate, ovarian and colon cancers. Determination of whether a given agent used in the treatment of cancer by reduction of IGFBP-2 and/or IGFBP-5 results in enhancement of clusterin expression can be readily determined using Northern blot or other techniques to detect clusterin mRNA or protein in the presence and absence of the agent. Those agents that result in enhanced clusterin expression may be made more effective through use in combination with an oligonucleotide inhibitor of clusterin expression Methods Administration of antisense ODNs can be carried out using the various mechanisms known in the art, including naked administration and administration in pharmaceutically acceptable lipid carriers. For example, lipid carriers for antisense delivery are disclosed in U.S. Pat. Nos. 5,855,911 and 5,417,978. In general, the antisense is administered by intravenous, intraperitoneal, subcutaneous or oral routes, or direct local tumor injection.

The amount of antisense ODN administered is one effective to reduce the expression of clusterin in cancer cells. It will be appreciated that this amount will vary both with the effectiveness of the antisense ODN employed, and with the nature of any carrier used. The determination of appropriate amounts for any given composition is within the skill in the art, through standard series of tests designed to assess appropriate therapeutic levels. In one embodiment, the antisense ODN is administered to a human patient in an amount of between 40-640 mg, or more particularly, from 300-640 mg. In another embodiment, the antisense ODN is administered according to the weight of the subject in need of the treatment. For example, the antisense ODN may be provided at a dosage of from 1 to 20 mg/kg of body weight.

The amount of and route of adminstration for the agent targeted to IGFBP-2 and/or IGFBP-5 will of course depend on the agent employed. In the case of antisense the amount administered is one effective to reduce the effective amount of levels of IGFBP-2 and/or IGFBP-5 in the endocrine-regulated tumor cell of concern. As noted above, in the context of the present invention, applicants do not intend to be bound by any specific mechanism by which this reduction may occur, although it is noted that the reduction may occur as a result of reduced expression of IGFBP-2 and -5 if the antisense molecule interferes with translation of the mRNA, or via an RNase mediated mechanism. Furthermore, it will be appreciated that the appropriate therapeutic amount will vary both with the effectiveness of the specific antisense oligonucleotide employed, and with the nature of any carrier used. The determination of appropriate amounts for any given composition is within the skill in the art, through standard series of tests designed to assess appropriate therapeutic levels.

Additional Therapeutic Agents

The method for treating cancer in accordance with one embodiment of the invention may further include administration of chemotherapy agents or other agents useful in breast cancer therapy and/or additional antisense ODNs directed at different targets in combination with the therapeutic effective to reduce the amount of active clusterin. For example, antisense clusterin ODN may be used in combination with more conventional chemotherapy agents such as taxanes (paclitaxel or docetaxel), mitoxanthrone, doxorubicin, gemcitabine, cyclophosphamide, decarbazine, topoisomerase inhibitors), angiogenesis inhibitors, differentiation agents and signal transduction inhibitors.

The application is further described in the following non-limiting examples.

EXAMPLES

Materials and Methods

Phosphorothioate oligonucleotides used in this study to target clusterin were purchased from La Jolla Pharmaceuticals Co. (La Jolla, Calif., USA) or provided by OncoGenex Technologies Inc., Vancouver, Canada. The sequence of the clusterin ASO used corresponded to the human clusterin translation initiation site (5'-CAGCAGCAGAGTCTTCAT-CAT-3') (SEQ ID NO.:4). A 2-base clusterin mismatch oligonucleotide (5'-CAGCAGCAGAGTATTTATCAT-3') (SEQ ID NO.: 20) was used as control. Oligonucleotides were delivered into cells in form of complexes with the Lipofectin™ transfection reagent (Invitrogen). Cells were incubated with different concentrations of oligonucleotides and Lipofectin™ for 6 hours in OPTIMEM™ medium (Gibco). At the end of oligonucleotide treatment, the medium was replaced with fresh growth medium containing 2% of fetal calf serum and at different time points, cells were processed according to the various analyses to be performed.

Example 1

LNCaP cells were treated with treated with 500 nM concentrations of antisense oligonucleotides of Seq. ID Nos. 45, 46 or 47 or a mismatch control. Levels of IGFBP-2 were measured. The results are summarized in FIG. 1A.

Figure 1B:
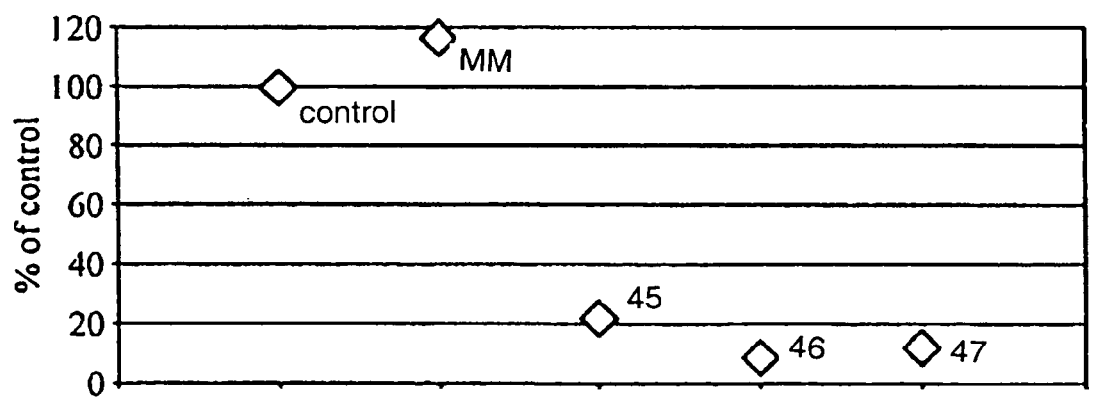

PC3 cells were treated with treated with 500 nM concentrations of antisense oligonucleotides of Seq. ID Nos. 45, 46 or 47 or a mismatch control. Levels of IGFBP-5 were measured. The results are summarized in FIG. 1B Example 2

Figure 2A:
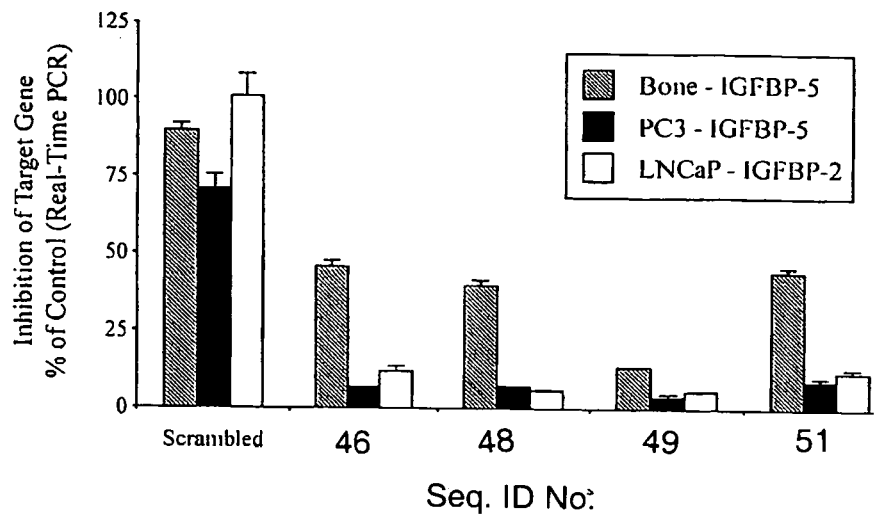
FIGS. 2A-E shows inhibition of IGFBP-2 and 5 in prostate cancer and bone cells using various antisense oligonucleotides.
Figure 2B:
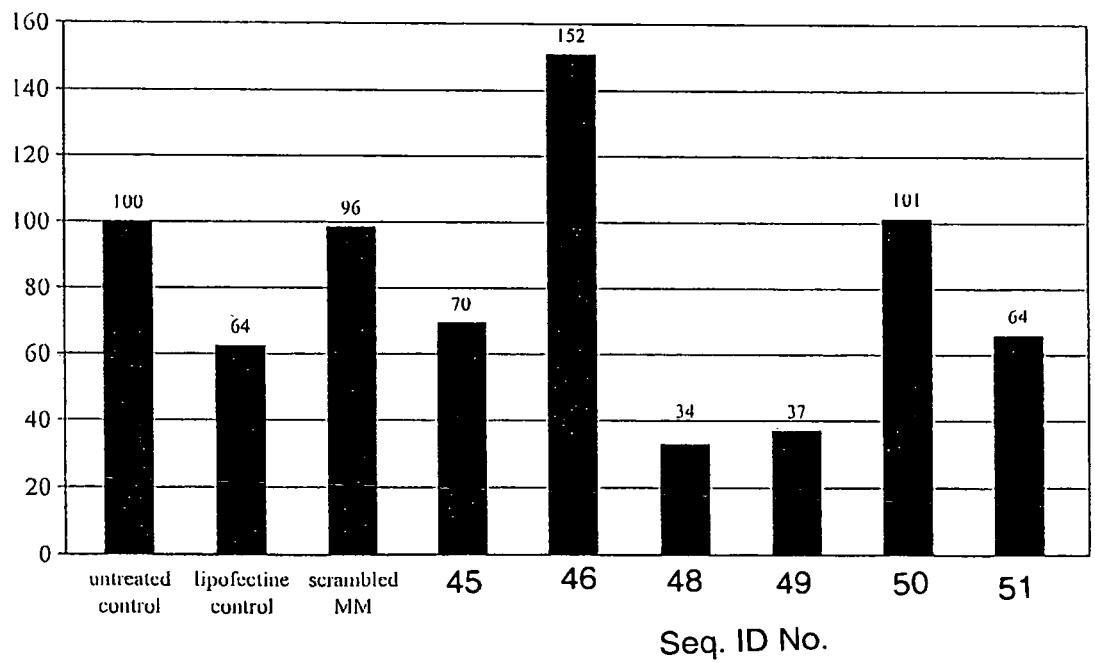
Figure 2C:
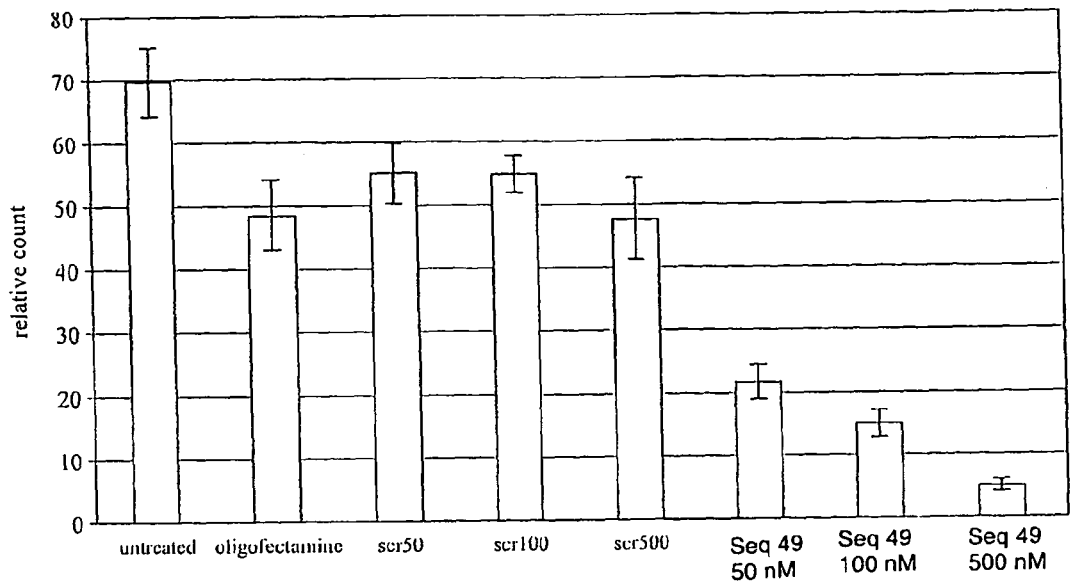
Figure 2D:
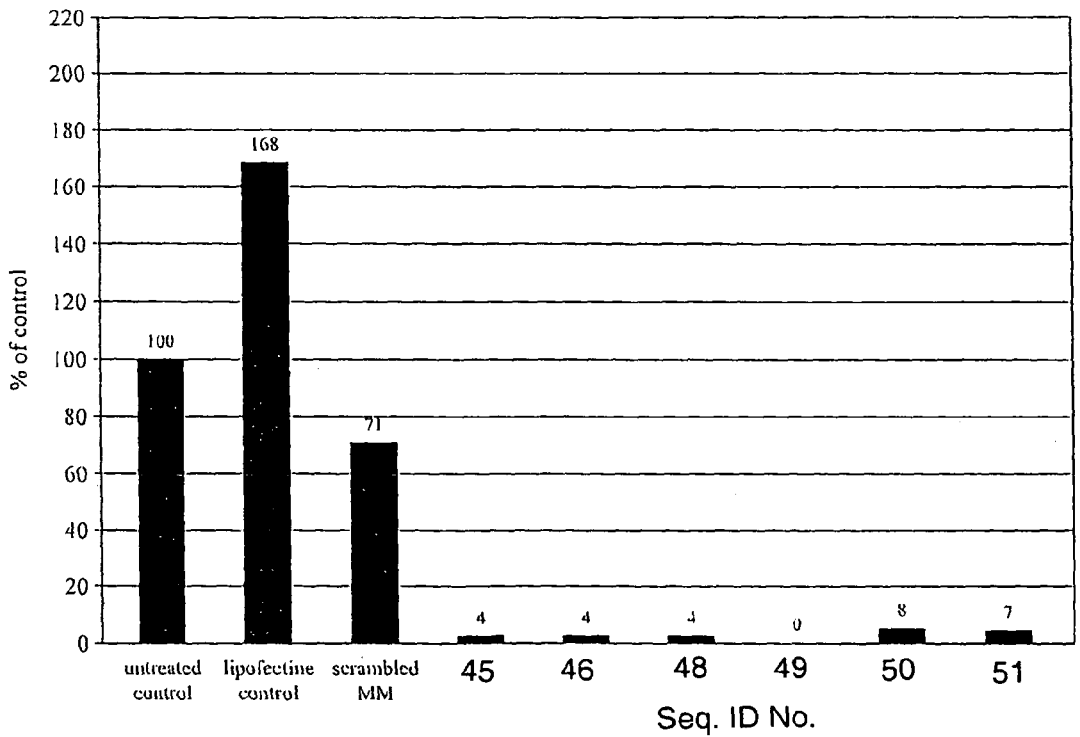
Figure 2E:
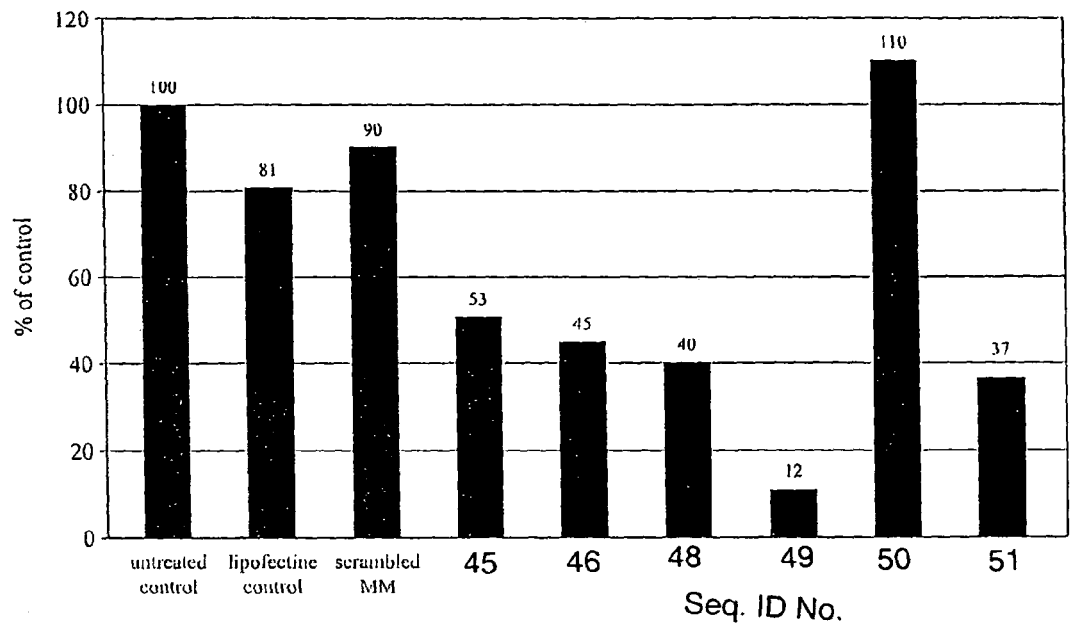

Bispecific antisense oligonucleotides were used to treat PC3, LNCaP and bone cells at concentration of 500 nm, and the amount of inhibition of IGFBP-2 or IGFBP-5 was measured using real time PCR. Oligonucleotides of Seq. ID Nos. 46, 48, 49 and 51 were tested, and all were effective to reduce the detected amount of the IGFBP measured. (FIG. 2A) Reductions of up to 70% in IGFBP-2 levels were also observed in A549 lung cells using 500 nM of Seq. ID Nos. 48 and 49. (FIG. 2B) Seq. ID No. 48 (500 nM) was also shown to be effective to inhibit cell growth of LNCaP cells and reduce the cell number by more than 90%. (FIG. 2C) FIGS. 2D and E respectively show results for inhibition of IGFBP-5 levels in PC3 cells with 500 nM of Seq ID Nos. 45, 46, 48, 49, 50 and 51; and inhibition of IGFBP-5 levels in human fetal bone fobroblast cells with 500 nM of Seq. ID Nos. 45, 46, 48, 49, 50 and 51.

Example 3

Figure 5:
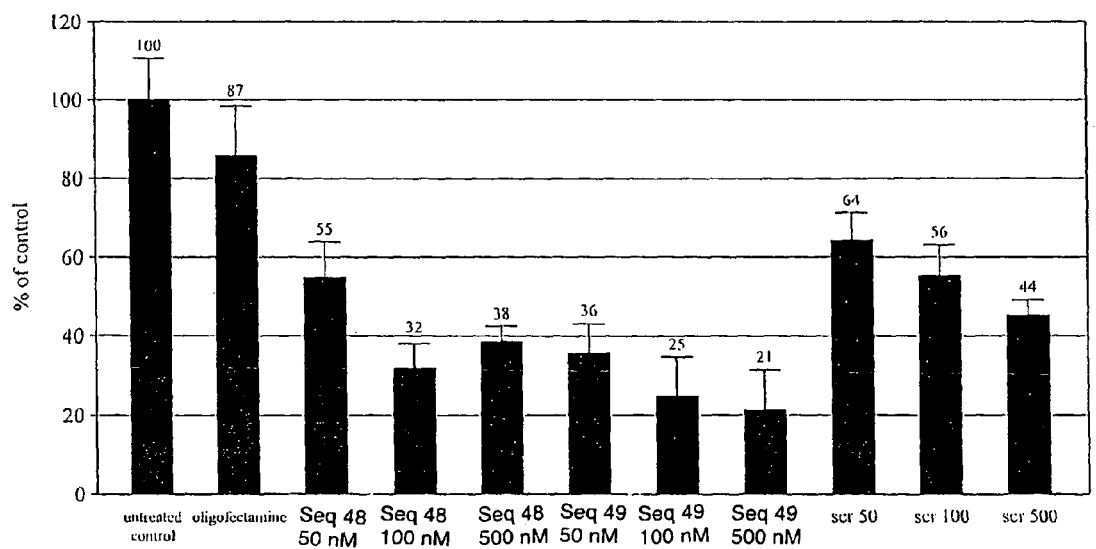
FIG. 5 shows results of real time PCR measurement of IGFBP-5 in MSF human fetal fibroblast cells after antisense treatment.

Real time PCR was used to measure the amount IGFBP-5 in MSF human fetal fibroblast cells after treatment with antisense oligonucleotide and LIPOFECTIN (4 µg/ml). Cells were plated in vitro and treated with a four-hour pulse of 500 nM oligonucleotide followd by a 20 hour period in normal medium plus 5% serum. A second four-hour pulse was repeated on day 2 and the cells were counted on day 3. The most active antisense oligonucleotides were Seq. ID Nos. 48 and 49. (FIG. 5)

Example 4

Figure 3:
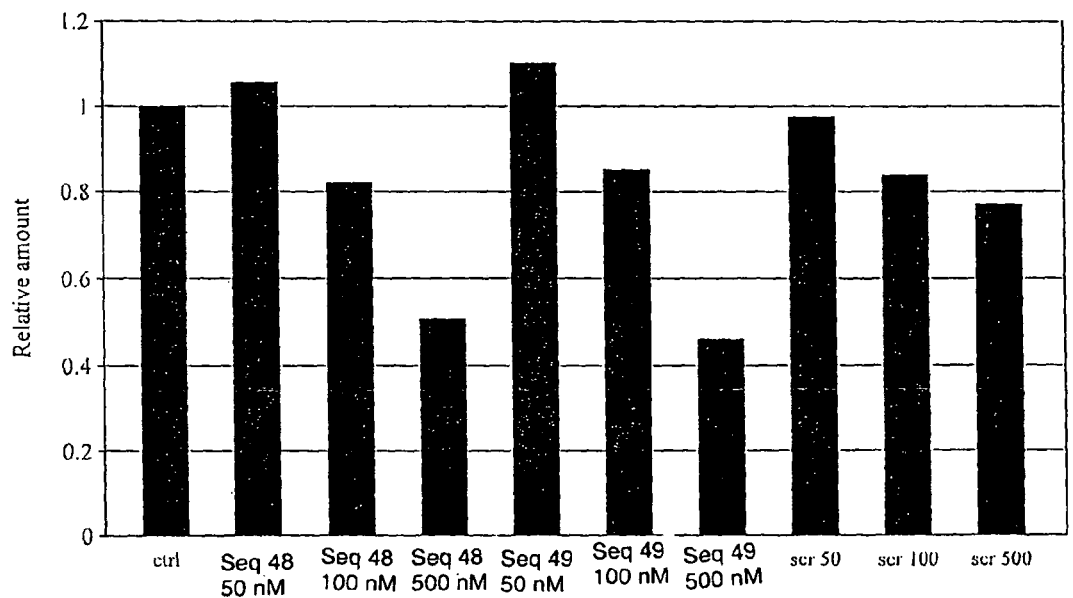
FIGS. 3 and 4 show real time PCR results for levels of IGFBP-2 and IGFBP-5 in RT4 bladder cancer cells after treatment with antisense oligonucleotides of the invention.
Figure 4:
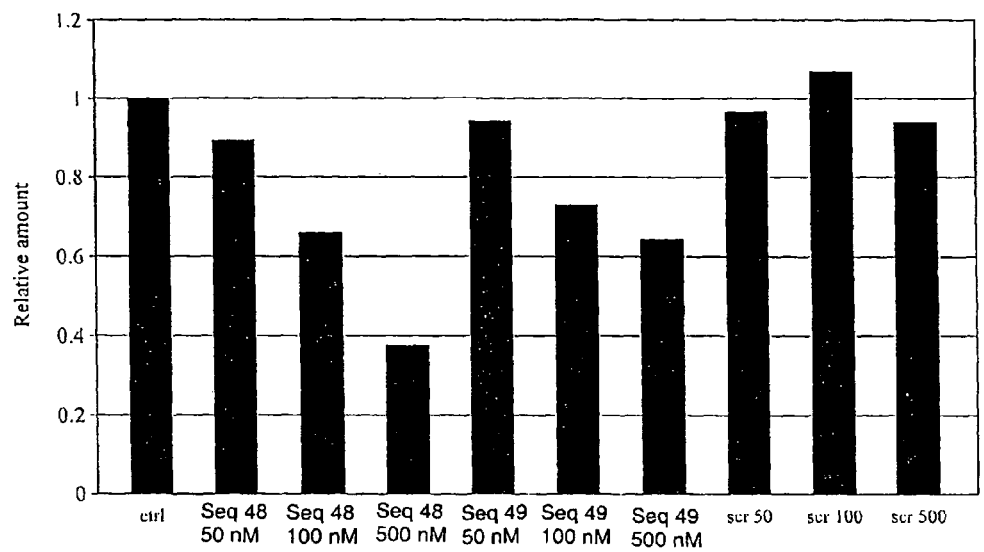

Real time PCR was used to evaluate the amounts of IGFBP-2 and IGFBP-5 in human bladder cancer (RT4) following treatment with varying amounts of antisense oligonucleotides (Seq. ID Nos. 48 and 49) and 4 µg/ml LIPOFECTIN. As shown in FIGS. 3 and 4, a dose dependent response was observed to both antisense oligonucleotides at concentrations ranging from 50 to 500 nM.

Example 5

Bispecific antisense (cagcagccgcagcccggctc, Seq. ID No. 49) targeted to IGFBP-2 and IGFBP-5 was found to induce apoptosis triggered expression of the stress-associated cytoprotective chaperone, clusterin in two prostate cancer cell lines. LNCaP and PC-3 cells were treated with the antisense and clusterin levels assessed by Western blotting. Full length clusterin was up-regulated by treatment with the bispecific antisense in PC-3 and LNCaP cells, while no significant changes were observed with control ODN. Endogenous clusterin expression in PC-3 cells increased by about 75%. Clusterin expression in LNCaP cells was almost undetectable under basal conditions, but increase >20 fold after treatment with the bispecific antisense.

Example 6

We next tested whether the bispecific antisense-induced up-regulation of clusterin could be inhibited using anti-clusterin antisense using a second generation MOE-gapmer ASO targeting the translation initiation site of clusterin (Seq. ID No. 4). PC-3 and LNCaP cells were treated with 100 nM of the bispecific antisense (its approximate IC50 in PC-3 and LNCaP cells), plus various concentrations of anti-clusterin antisense or control ODN, and clusterin levels were analyzed by Western blotting. In both cell lines, bispecific-antisense-induced up-regulation of clusterin was significantly inhibited by the anti-clusterin antisense.

Example 7

Figure 6A:
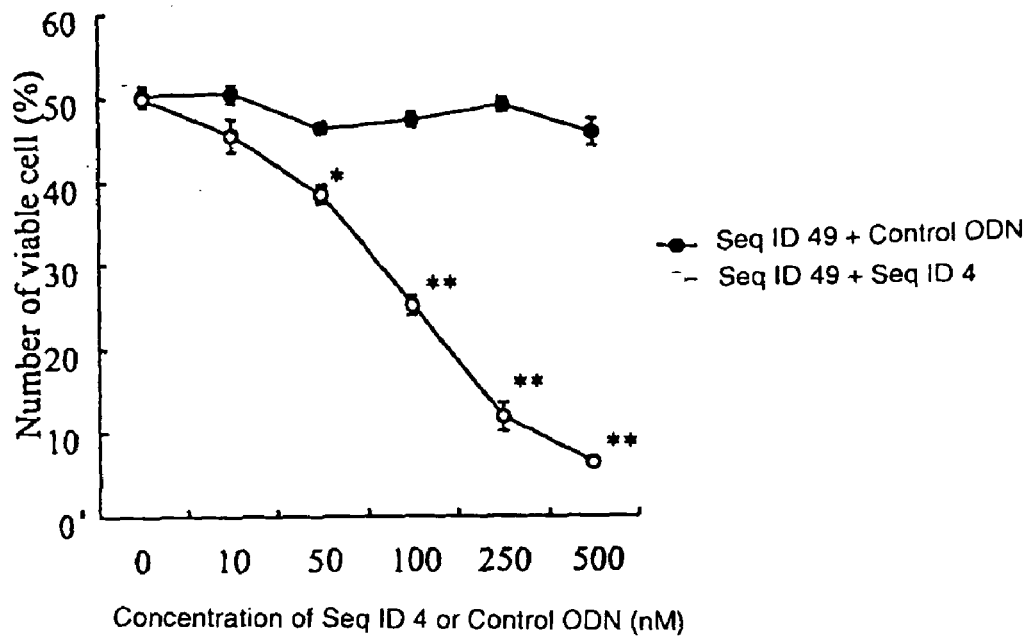
FIGS. 6 A-D show results for combination therapy using a bispecific antisense targeting both IGFBP-2 and IGFBP-5 and anti-clusterin antisense.
Figure 6B:
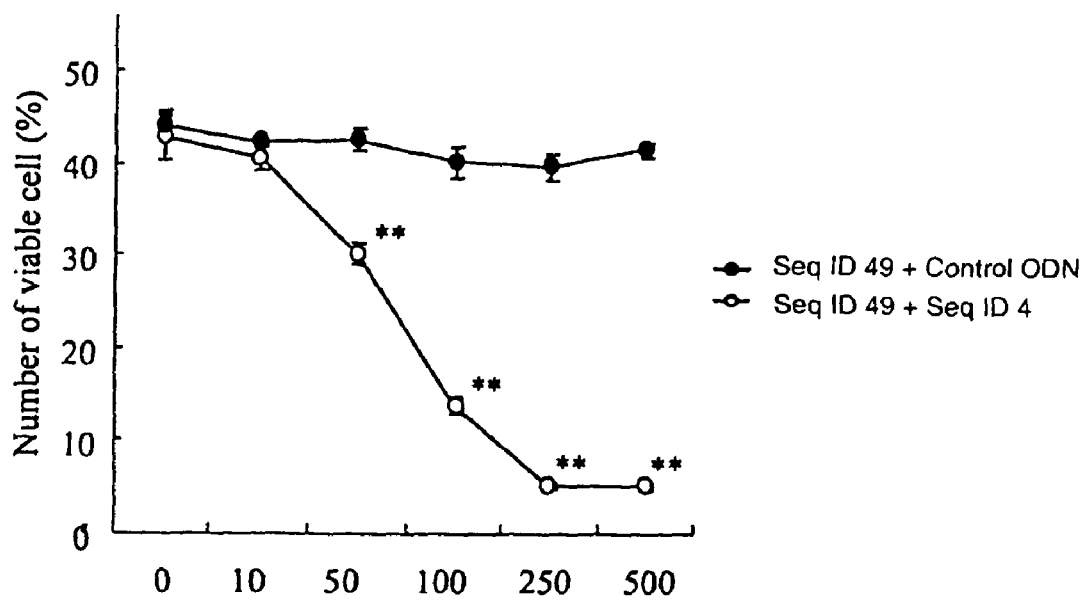
Figure 6C:
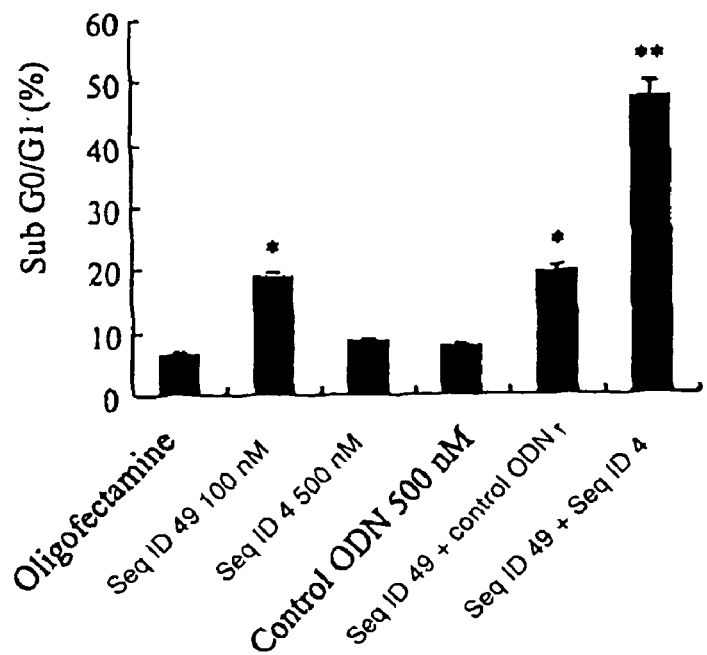
Figure 6D:
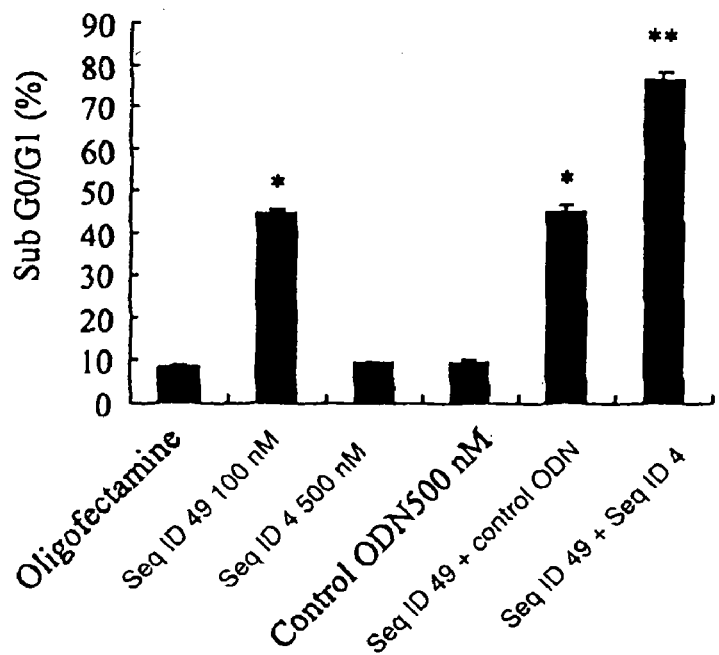

We next tested whether anti-clusterin antisense knockdown of bispecific antisense-induced increases in clusterin enhanced apoptotic rates. PC-3 and LNCaP cells were treated daily with 100 nM of the bispecific antisense and various concentrations of anti-clusterin antisense or control ODN for 2 days. After 72 hours incubation, cell viability was determined by the MTT or crystal violet assay, respectively. As shown in FIG. 6, A and B, the combination with the anti-clusterin antisense significantly enhanced the cytotoxicity of the bispecific antisense in a dose-dependent manner in both PC-3 and LNCaP cells. In contrast, the anti-clusterin antisense had no effects on apoptotic rates when used alone. Combined treatment of bispecific antisense plus anti-clusterin antisense significantly increased the sub G0/G1 fraction compared to controls in both PC-3 and LNCaP cells (FIG. 6C and D). We further evaluated the effects of combined treatment on apoptosis using Western blot analysis to identify PARP cleavage, a substrate for caspases activated during apoptotic execution (Lazebnik et al. *Nature* 371: 346-347 (1994). In PC-3 cells the 85 kD PARP cleaved fragment was detected only after combined treatment with >100 nM of anti-clusterin antisense treatment. Similarly, increased levels of cleaved PARP was detected in LNCaP cells after treatment with bispecific antisense plus >100 nM anti-clusterin antisense.

Example 8

Figure 7A:
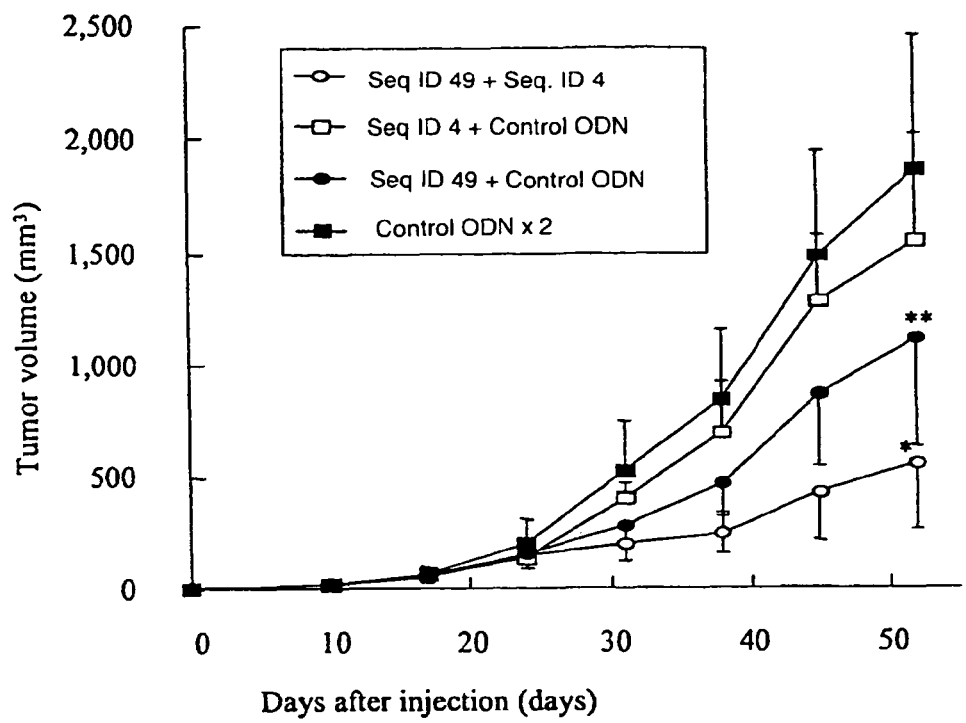
FIGS. 7 A-C shows results for treatment of PC-3 cells with combination therapy using a bispecific antisense targeting both IGFBP-2 and IGFBP-5 and anti-clusterin antisense.
Figure 7B:
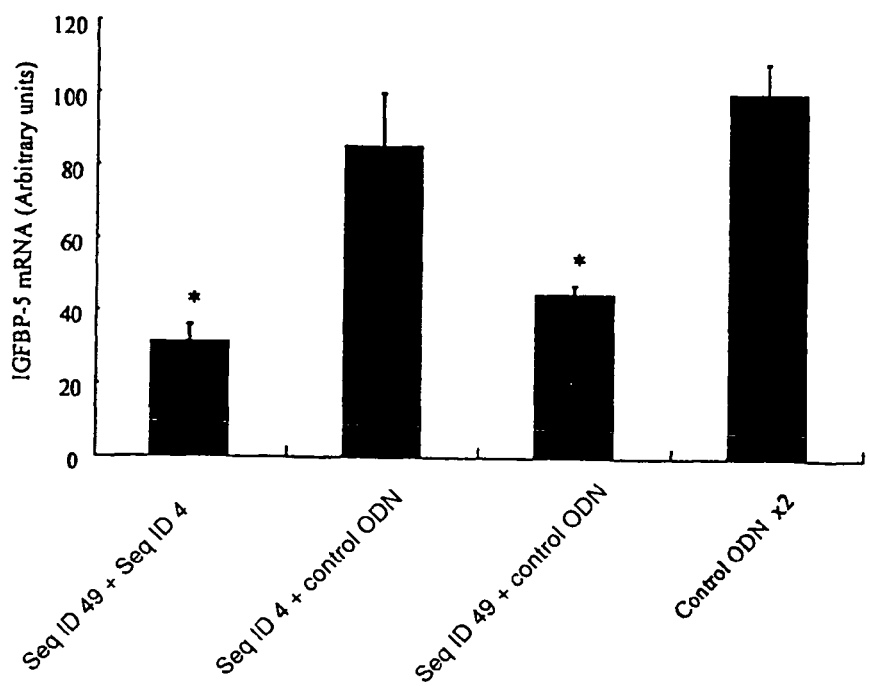
Figure 7C:
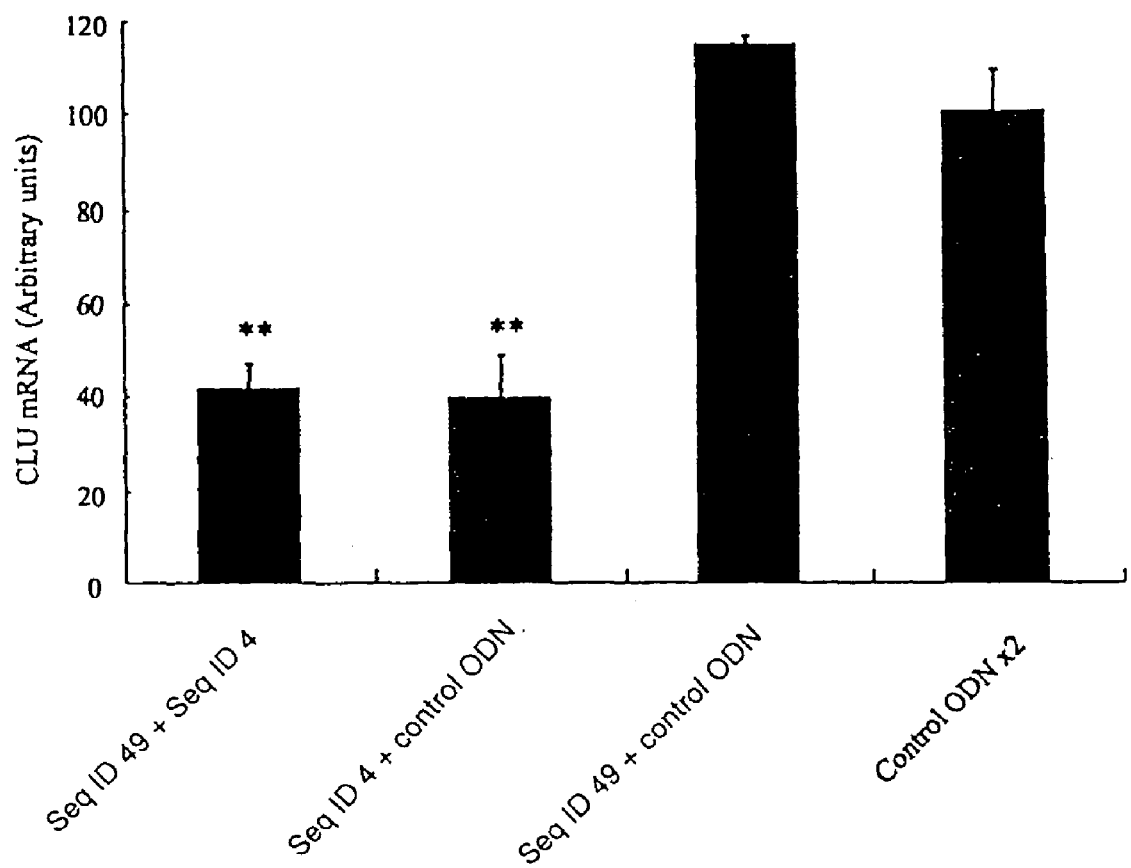
Figure 8A:
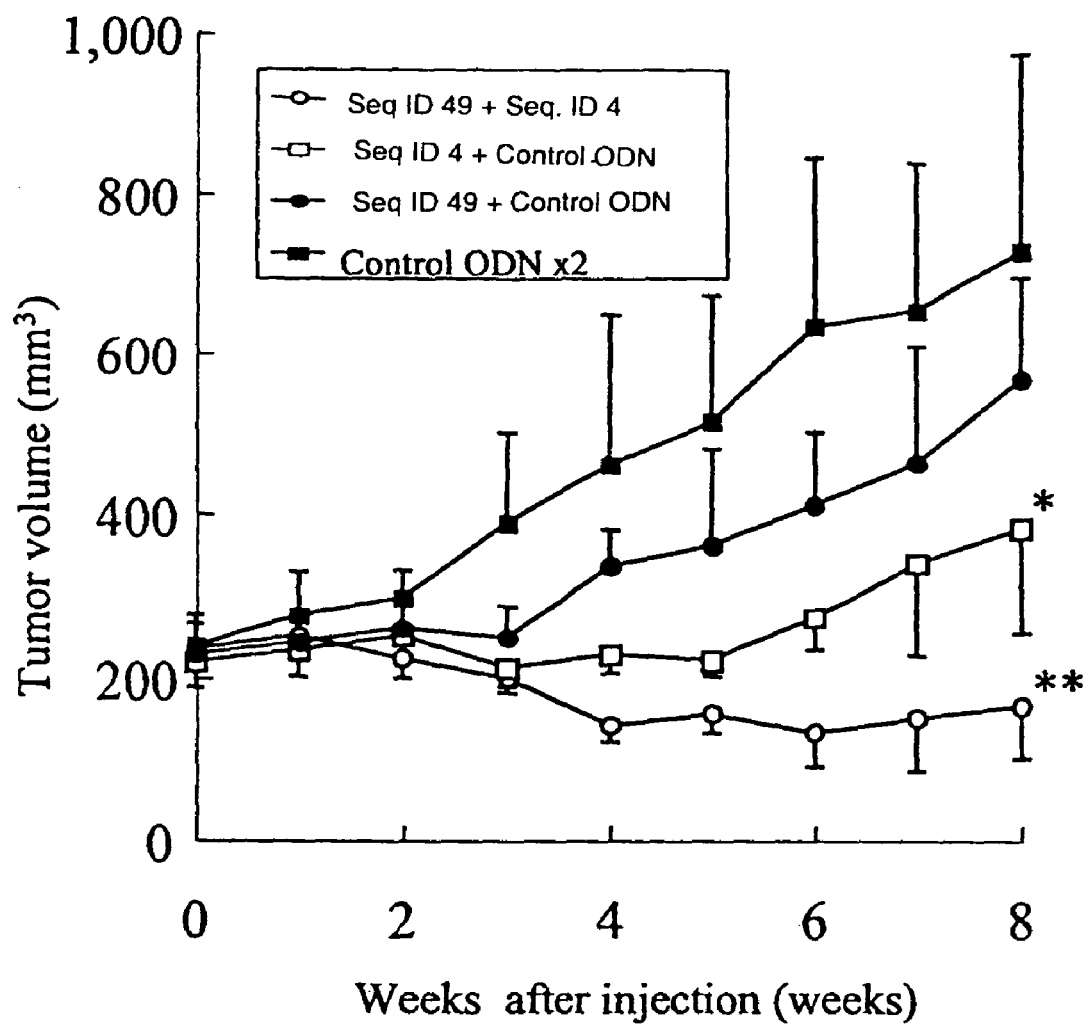
FIGS. 8A-E shows results for treatment of PC-3 cells with combination therapy using a bispecific antisense targeting both IGFBP-2 and IGFBP-5 and anti-clusterin antisense.
Figure 8B:
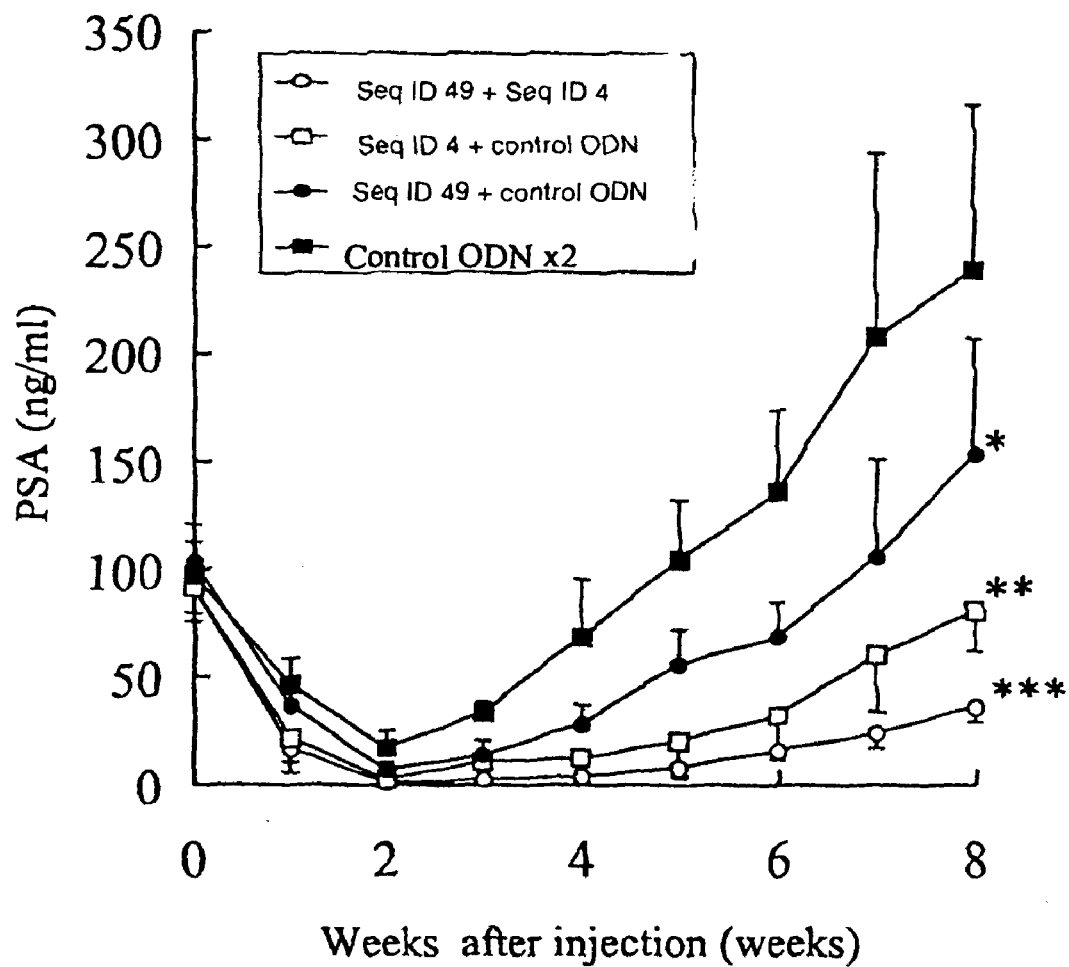
Figure 8C:
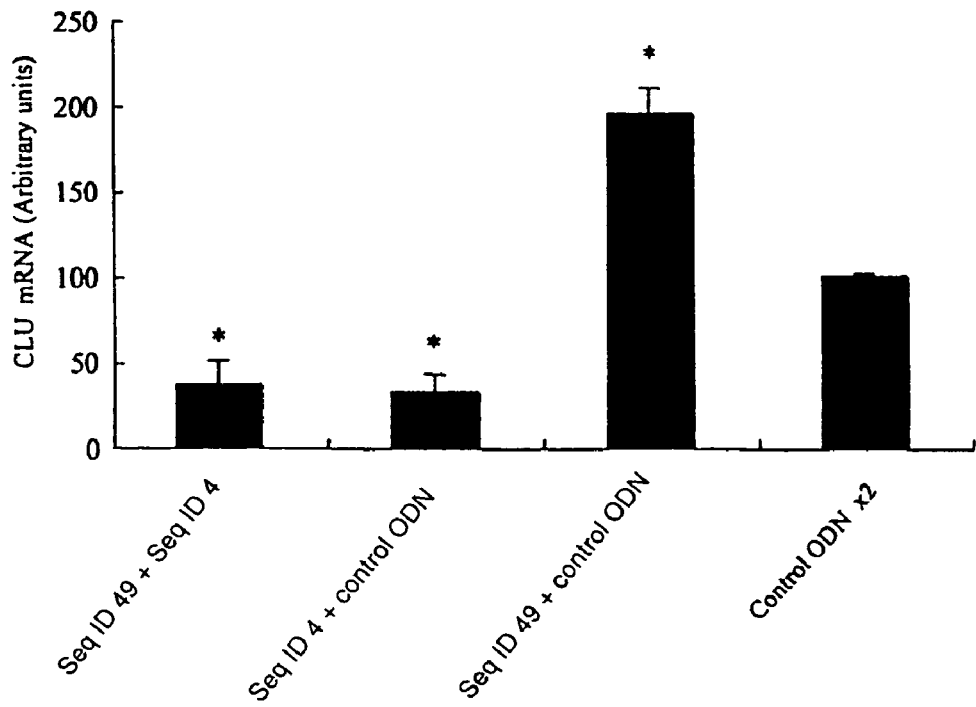
Figure 8D:
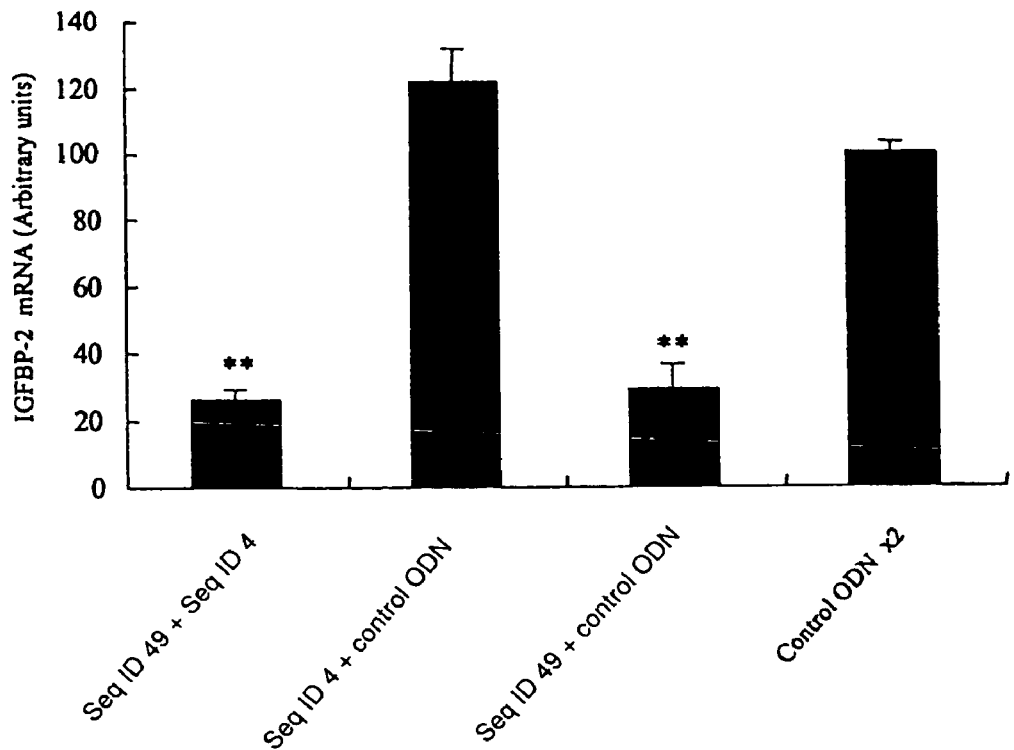
Figure 8E:
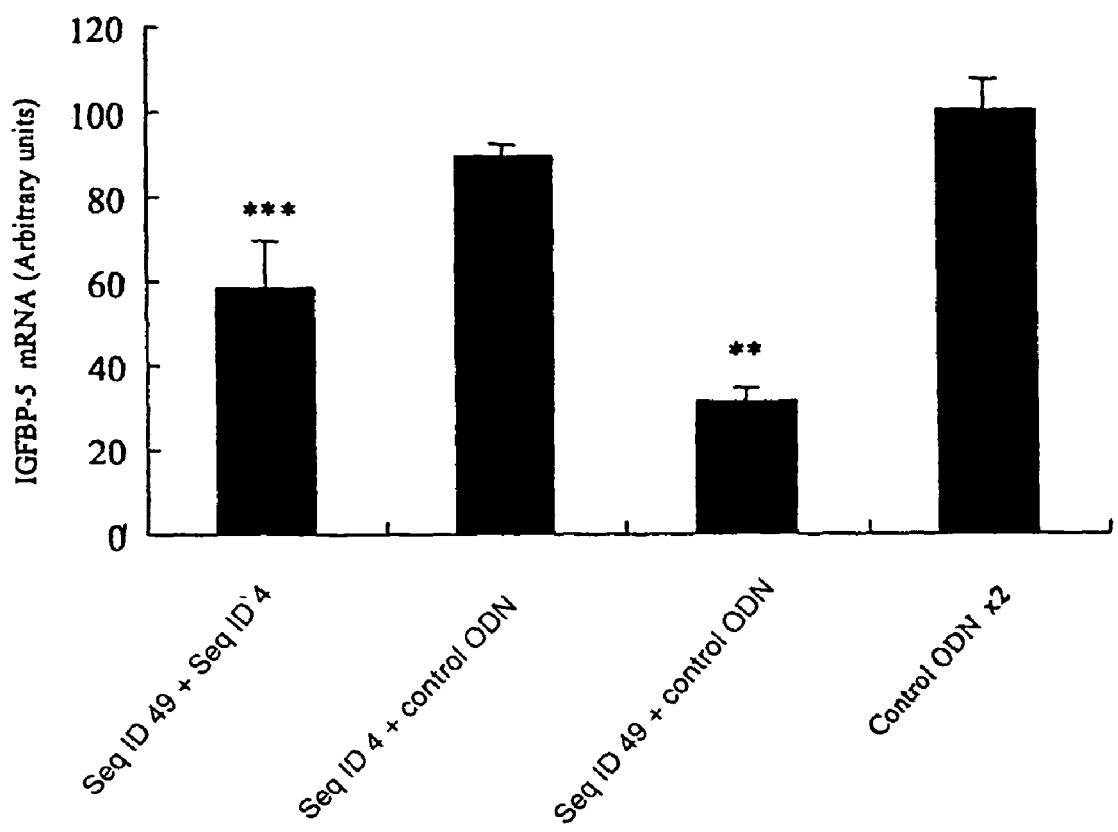

We next tested whether the in vitro observations above could be recapitulated in vivo. Male mice bearing PC-3 tumors (100 mm$^3$) were randomly selected for treatment with bispecific antisense plus anti-clusterin antisense, anti-clusterin antisense plus control ODN, bispecific antisense plus control ODN or control ODN alone. Each treatment group consisted of 10 mice and each mouse received 12.5 mg/kg of bispecific antisense, anti-clusterin antisense and/or control ODN administered once daily by i.p. during the first week and 3 times per week thereafter. Treatments were continued for 5 weeks after starting ASO injection. Under this experimental condition, no adverse effects were observed. As shown in FIG. 7A, bispecific antisense plus control ODN treatment reduced PC-3 tumor volume by 41% compared to control ODN alone (p<0.05), whereas no significant difference was observed between anti-clusterin antisense plus control ODN or control ODN alone treatment groups. Combined treatment of bispecific antisense plus anti-clusterin antisense significantly inhibited PC-3 tumor growth by 52, 64 and 71% compared to bispecific antisense, anti-clusterin antisense and control ODN treatment groups, respectively. Total RNA was extracted from each tumor after sacrifice and assessed for changes in mRNA levels of IGFBP-5 and clusterin using Northern blot analysis. As shown in FIGS. 7B and C, mRNA levels of IGFBP-5 in PC-3 tumors were significantly reduced by bispecific antisense containing treatment regimen when compared to other treatment regimens. Similarly, mRNA levels of clusterin in PC-3 tumors were significantly reduced by anti-clusterin antisense containing regimen compared to other treatment regimens. Clusterin mRNA level was increased after treatment with bispecific antisense plus control ODN by 15% compared to control ODN alone. Mice bearing subcutaneous LNCaP tumors were castrated and treated with the same schedule described above for PC-3 tumors. Each treatment group consisted of 10 mice. As shown in FIG. 8A, anti-clusterin antisense plus control ODN treatment significantly reduced LNCaP tumor volume by 47% compared to control ODN alone (p<0.01). Although bispecific antisense plus control ODN treatments reduced LNCaP tumor volume by 22% compared to control ODN alone, the difference did not reached statistical significance. Combined treatment with bispecific antisense and anti-clusterin antisense significantly inhibited LNCaP tumor growth by 61, 57 and 77% compared to bispecific antisense, anti-clusterin antisense and control ODN treatment groups, respectively. Serum PSA decreased by approximately 80% by 2 weeks in all treatment groups after castration, and then increased in the control ODN and bispecific antisense plus control ODN groups by 2.5- and 1.5-fold, respectively by 8 weeks post castration. Serum PSA in anti-clusterin antisense plus control ODN and anti-clusterin antisense plus bispecific antisense treatment group remained below baseline levels for longer than 8 weeks post treatment (FIG. 8B). Total RNA was extracted from each tumor after sacrifice and assessed for changes in mRNA levels of clusterin, IGFBP-2 and IGFBP-5 using Northern blot analysis. As shown in FIG. 8, C, D, and E, mRNA levels of clusterin in LNCaP tumors were significantly reduced by anti-clusterin antisense containing regimen compared to other treatment regimens. Similarly, mRNA levels of IGFBP-2 and IGFBP-5 in LNCaP tumors were significantly decreased by bispecific antisense containing treatment regimen when compared to other treatment regimens. Clusterin mRNA level was significantly increased after treatment with bispecific antisense plus control ODN by 2-fold compared to control ODN alone. These data, observed both in PC-3 and LNCaP tumor model, mirror the in vitro observations above, with bispecific antisense-induced up-regulation of clusterin and anti-clusterin antisense mediated suppression of bispecific antisense-induced clusterin up-regulation.

All of the cited documents are incorporated herein by reference in those jurisdictions allowing such incorporation.

While specific embodiments of the invention have been described and illustrated, such embodiments should be considered illustrative of the invention only and not as limiting the invention.

REFERENCES

1. Wong et al., *Eur. J. Biochem.* 221 (3), 917-925 (1994)
2. Sensibar et al., *Cancer Research* 55: 2431-2437 (1995)
3. Fire et al. (1998) *Nature* 391, 806-811
4. Carthew et al. (2001) Current Opinions in Cell Biology 13, 244-248.

---

The invention claimed is:

1. A therapeutic combination comprising
   (a) a bispecific oligonucleotide agent that reduces both IGFBP-2 and IGFBP-5 and
   (b) an oligonucleotide effective to reduce the effective amount of clusterin in cancer cells.

2. The combination of claim 1, wherein the oligonucleotide effective to reduce the amount of clusterin is an anti-clusterin antisense oligonucleotide.

3. The combination of claim 2, wherein said anti-clusterin antisense oligonucleotide spans either the translation initiation site or the termination site of clusterin.

4. The combination of claim 3 wherein said anti-clusterin antisense oligonucleotide is modified to enhance in vivo stability relative to an unmodified oligonucleotide of the same sequence.

5. The combination of claim 4, wherein said modification is a (2'-O-(2-methoxyethyl) modification.

6. The combination of claim 5, wherein said antisense oligonucleotide has a phosphorothioate backbone throughout, the sugar moieties of nucleotides 1-4 and 18-21, the "wings", bear 2'-O-methoxyethyl modifications and the remaining nucleotides are 2'-deoxynucleotides.

7. The combination of claim 6, wherein said anti-clusterin antisense oligonucleotide consists essentially of an oligonucleotide selected from the group consisting of Seq. ID. Nos.: 2 to 19.

8. The combination of claim 7, wherein the agent that reduces both IGFBP-2 and IGFBP-5 is an oligodeoxynucleotide and wherein substantially all of the oligodeoxynucleotide is complementary to a portion of a gene encoding human IGFBP-2 and substantially all of the oligodeoxynucleotide is also complementary to a portion of a gene encoding human IGFBP-5.

9. The combination of claim 8, wherein the oligodeoxynucleotide consists of a sequence selected from among Seq. ID Nos 45-51.

10. The combination of claim 6, wherein said anti-clusterin antisense oligonucleotide consists essentially of an oligonucleotide selected from the group consisting of Seq. ID. No. 4, Seq. ID. No. 5 and Seq. ID. No. 12.

11. The combination of claim 10, wherein the agent that reduces both IGFBP-2 and IGFBP-5 is an oligodeoxynucleotide and wherein substantially all of the oligodeoxynucleotide is complementary to a portion of a gene encoding human IGFBP-2 and substantially all of the oligodeoxynucleotide is also complementary to a portion of a gene encoding human IGFBP-5.

12. The combination of claim 11, wherein the oligodeoxynucleotide consists of a sequence selected from among Seq. ID Nos 45-51.

13. The combination of claim 1, wherein the agent that reduces both IGFBP-2 and IGFBP-5 is an oligodeoxynucleotide and wherein substantially all of the oligodeoxynucleotide is complementary to a portion of a gene encoding human IGFBP-2 and substantially all of the oligodeoxynucleotide is also complementary to a portion of a gene encoding human IGFBP-5.

14. The combination of claim 13, wherein the oligodeoxynucleotide consists of a sequence selected from among Seq. ID Nos 45-51.

15. The combination of claim 3, wherein the oligonucleotide that reduces the amount of clusterin is an siRNA.

16. The combination claim 1, wherein the agent that reduces both IGFBP-2 and IGFBP-5 and the oligonucleotide effective to reduce the amount of clusterin are each provided in dosage unit form, either together or individually.

17. The combination of claim 1, wherein the agent that reduces both IGFBP-2 and IGFBP-5 is an oligonucleotide consisting essentially of the sequence as set forth in Seq ID No. 49, and the oligonucleotide effective to reduce the effective amount of clusterin in the cancer cells consists essentially of the sequence as set forth in Seq. ID No. 4.

18. The combination of claim 17, wherein the agent that reduces both IGFBP-2 and IGFBP-5 and the oligonucleotide effective to reduce the amount of clusterin are each provided in dosage unit form, either together or individually.

19. The combination of claim 13, wherein said anti-clusterin antisense oligonucleotide consists essentially of an oligonucleotide selected from the group consisting of Seq. ID. No. 4, Seq. ID. No. 5 and Seq. ID. No. 12.

20. The combination of claim 19, wherein the oligodeoxynucleotide that reduces both IGFBP-2 and IGFBP-5 consists of a sequence selected from among Seq. ID Nos 45-51.

21. The combination of claim 1, wherein the oligodeoxynucleotide that reduces both IGFBP-2 and IGFBP-5 consists of Seq ID No. 49, and the oligonucleotide that reduces clusterin consist of Seq ID No. 4.

* * * * *

UNITED STATES PATENT AND TRADEMARK OFFICE
CERTIFICATE OF CORRECTION

PATENT NO. : 7,973,017 B2
APPLICATION NO. : 11/287334
DATED : July 5, 2011
INVENTOR(S) : Martin Gleave It is certified that error appears in the above-identified patent and that said Letters Patent is hereby corrected as shown below:

In the Specification

In Column 6, TABLE 1 should read:

| Seq ID No. | Description | SEQUENCE (5' to 3') |
| --- | --- | --- |
| 2 | Antisense TRPM-2 oligonucleotide | GCACAGCAGGAGAATCTTCAT |
| 3 | Antisense TRPM-2 oligonucleotide | TGGAGTCTTTGCACGCCTCGG |
| 4 | Antisense oligonucleotide corresponding to the humanTRPM-2 translation initiation site | CAGCAGCAGAGTCTTCATCAT |
| 5 | Antisense TRPM-2 oligonucleotide | ATTGTCTGAGACCGTCTGGTC |
| 6 | Antisense TRPM-2 oligonucleotide | CCTTCAGCTTTGTCTCTGATT |
| 7 | Antisense TRPM-2 oligonucleotide | AGCAGGGAGTCGATGCGGTCA |
| 8 | Antisense TRPM-2 oligonucleotide | ATCAAGCTGCGGACGATGCGG |
| 9 | Antisense TRPM-2 oligonucleotide | GCAGGCAGCCCGTGGAGTTGT |
| 10 | Antisense TRPM-2 oligonucleotide | TTCAGCTGCTCCAGCAAGGAG |
| 11 | Antisense TRPM-2 oligonucleotide | AATTTAGGGTTCTTCCTGGAG |
| 12 | Antisense TRPM-2 oligonucleotide | GCTGGGCGGAGTTGGGGCCT |

Signed and Sealed this
Twenty-fifth Day of August, 2015

Michelle K. Lee
*Director of the United States Patent and Trademark Office*

| | | |
|---|---|---|
| 20 | 2 base TRPM-2 mismatch oligonucleotide used as a control -- | CAGCAGCAGAGTATTTATCAT |

In Column 6, lines 3-5 should read: -- consisting of Seq. ID. Nos.: 2 to 12 as shown in Table 1, or more specifically Seq. ID. No. 4, Seq. ID. No. 5 and Seq. ID. No. 12. --

In the Claims

In Column 35, Claim 7, lines 56-57 should read: -- nucleotide selected from the group consisting of Seq. ID. Nos.: 2 to 12. --